(12) United States Patent
Jacobs et al.

(10) Patent No.: US 11,844,552 B2
(45) Date of Patent: Dec. 19, 2023

(54) SURGICAL DEVICE FOR SPINAL FIXATION

(71) Applicant: Medos International Sarl, Le Locle (CH)

(72) Inventors: Samuel Jacobs, Acton, MA (US); Mark Hall, Bridgewater, MA (US)

(73) Assignee: Medos International Sarl, Le Locle (CH)

( * ) Notice: Subject to any disclaimer, the term of this patent is extended or adjusted under 35 U.S.C. 154(b) by 357 days.

(21) Appl. No.: 17/128,711

(22) Filed: Dec. 21, 2020

(65) Prior Publication Data

US 2021/0106363 A1 Apr. 15, 2021

Related U.S. Application Data

(63) Continuation of application No. 16/262,549, filed on Jan. 30, 2019, now Pat. No. 10,869,696.

(51) Int. Cl.
*A61B 17/70* (2006.01)

(52) U.S. Cl.
CPC ...... *A61B 17/7053* (2013.01); *A61B 17/7047* (2013.01); *A61B 17/7001* (2013.01)

(58) Field of Classification Search
CPC ............ A61B 17/7022; A61B 17/7032; A61B 17/7034; A61B 17/7047; A61B 17/7056; A61B 17/707
See application file for complete search history.

(56) References Cited

U.S. PATENT DOCUMENTS

| 4,611,582 | A | 9/1986 | Duff |
| 5,122,131 | A | 6/1992 | Tsou |
| 5,246,442 | A | 9/1993 | Ashman et al. |
| 5,257,993 | A | 11/1993 | Asher et al. |
| 5,263,954 | A | 11/1993 | Schlapfer et al. |
| 5,304,178 | A | 4/1994 | Stahurski |
| 5,403,314 | A | 4/1995 | Currier |
| 5,413,576 | A | 5/1995 | Rivard |
| 5,476,464 | A | 12/1995 | Metz-Stavenhagen et al. |
| 5,584,832 | A | 12/1996 | Schlaepfer |
| 5,772,663 | A | 6/1998 | Whiteside et al. |

(Continued)

FOREIGN PATENT DOCUMENTS

WO 2015092300 A1 6/2015

OTHER PUBLICATIONS

Invitation to Pay Additional Fees Received received for PCT Application No. PCT/IB2020/050707, dated Apr. 28, 2020, 13 pages.

(Continued)

*Primary Examiner* — Eduardo C Robert
*Assistant Examiner* — Michelle C Eckman
(74) *Attorney, Agent, or Firm* — William C. Geary

(57) ABSTRACT

Surgical instruments, methods, and systems are provided for securing spinal fixation elements to bone. For example, a spinal fixation system is provided that has a receiver with proximal and distal ends. The proximal end of the receiver is configured to receive various fixation members, such as spinal rods and set screws, therein. The distal end of the receiver has a hook member that is operably coupled thereto and has an opening that is configured to receive bone therein. The hook member is configured to be secured to bone without penetrating the bone.

17 Claims, 14 Drawing Sheets

(56) References Cited

U.S. PATENT DOCUMENTS

| | | |
|---|---|---|
| 5,989,251 A | 11/1999 | Nichols |
| 6,126,660 A | 10/2000 | Dietz |
| 6,302,888 B1 | 10/2001 | Mellinger et al. |
| 6,387,097 B1 | 5/2002 | Alby |
| 6,514,255 B1 | 2/2003 | Ferree |
| 6,589,243 B1 | 7/2003 | Viart et al. |
| 6,605,091 B1 | 8/2003 | Iwanski |
| 6,749,361 B2 | 6/2004 | Hermann et al. |
| 7,011,659 B2 | 3/2006 | Lewis et al. |
| 7,959,655 B2 | 6/2011 | Kawakami et al. |
| 9,283,084 B1 | 3/2016 | O'Hara |
| 9,402,652 B1 | 8/2016 | Aslie |
| 9,622,789 B2 | 4/2017 | Carbone |
| 10,420,590 B2 | 9/2019 | Le Couedic et al. |
| 10,543,023 B2 | 1/2020 | Le Couedic et al. |
| 10,595,904 B2 | 3/2020 | Albert et al. |
| 10,869,696 B2 | 12/2020 | Jacobs et al. |
| 2001/0034522 A1 | 10/2001 | Frigg |
| 2002/0040222 A1 | 4/2002 | Hashimoto et al. |
| 2003/0045876 A1* | 3/2003 | Stahurski ........... A61B 17/7056 606/276 |
| 2003/0109881 A1 | 6/2003 | Shirado et al. |
| 2003/0130659 A1 | 7/2003 | Haider |
| 2003/0187437 A1 | 10/2003 | Ginsburg |
| 2004/0064140 A1 | 4/2004 | Taylor et al. |
| 2004/0111091 A1 | 6/2004 | Ogilvie et al. |
| 2005/0228375 A1 | 10/2005 | Mazda et al. |
| 2005/0277929 A1 | 12/2005 | Raiszadeh |
| 2006/0015099 A1 | 1/2006 | Cannon et al. |
| 2006/0100707 A1 | 5/2006 | Stinson et al. |
| 2006/0229607 A1 | 10/2006 | Brumfield |
| 2006/0293660 A1 | 12/2006 | Lewis et al. |
| 2007/0016189 A1* | 1/2007 | Lake .................. A61B 17/7047 606/250 |
| 2007/0072459 A1* | 3/2007 | Stahurski ........... A61B 17/7047 439/135 |
| 2007/0161990 A1* | 7/2007 | Hillyard ............. A61B 17/7034 606/86 A |
| 2007/0288013 A1 | 12/2007 | Sanders |
| 2008/0058818 A1 | 3/2008 | Schwab |
| 2009/0131982 A1 | 5/2009 | Schwab |
| 2009/0202387 A1 | 8/2009 | Dlugos, Jr. et al. |
| 2009/0318974 A1 | 12/2009 | Yuan et al. |
| 2010/0160981 A1 | 6/2010 | Butler et al. |
| 2011/0060367 A1 | 3/2011 | Stauber |
| 2011/0087288 A1 | 4/2011 | Stevenson et al. |
| 2011/0112581 A1 | 5/2011 | Clement |
| 2011/0144694 A1 | 6/2011 | Laeng et al. |
| 2011/0245875 A1 | 10/2011 | Karim |
| 2011/0301644 A1 | 12/2011 | Belliard |
| 2012/0065683 A1 | 3/2012 | Kuo et al. |
| 2012/0130373 A1 | 5/2012 | Larroque-Lahitette |
| 2012/0215268 A1* | 8/2012 | Stahurski ........... A61B 17/7056 606/86 R |
| 2012/0253409 A1 | 10/2012 | Peterson et al. |
| 2013/0023878 A1 | 1/2013 | Belliard et al. |
| 2013/0041410 A1 | 2/2013 | Hestad et al. |
| 2013/0072983 A1 | 3/2013 | Lindquist et al. |
| 2013/0231704 A1* | 9/2013 | Larroque-Lahitette ..................... A61B 17/7032 606/279 |
| 2013/0304129 A1 | 11/2013 | Hawkins et al. |
| 2014/0094850 A1 | 4/2014 | Clement et al. |
| 2014/0114356 A1 | 4/2014 | Le Couedic et al. |
| 2014/0148854 A1 | 5/2014 | Carlson et al. |
| 2014/0243905 A1 | 8/2014 | Cavallazzi et al. |
| 2014/0257397 A1 | 9/2014 | Akbarnia et al. |
| 2014/0277149 A1 | 9/2014 | Rooney et al. |
| 2014/0277155 A1 | 9/2014 | Barrus et al. |
| 2014/0277207 A1 | 9/2014 | Baccelli et al. |
| 2014/0303672 A1 | 10/2014 | Tran et al. |
| 2014/0343612 A1 | 11/2014 | Rezach et al. |
| 2015/0342646 A1 | 12/2015 | Wessels et al. |
| 2016/0008007 A1 | 1/2016 | Taha |
| 2016/0015430 A1 | 1/2016 | Buttermann |
| 2016/0106478 A1 | 4/2016 | Simpson et al. |
| 2016/0242819 A1 | 8/2016 | Simpson et al. |
| 2016/0262806 A1 | 9/2016 | Hsu et al. |
| 2016/0296254 A1 | 10/2016 | Dimar, II |
| 2017/0086888 A1 | 3/2017 | Simpson et al. |
| 2017/0086889 A1 | 3/2017 | Padilla et al. |
| 2017/0135733 A1 | 5/2017 | Donner et al. |
| 2017/0172633 A1 | 6/2017 | Simpson |
| 2017/0181772 A1 | 6/2017 | Buttermann |
| 2017/0258497 A1 | 9/2017 | Unger et al. |
| 2017/0281246 A1 | 10/2017 | Murray et al. |
| 2018/0014857 A1 | 1/2018 | Albert et al. |
| 2018/0064469 A1 | 3/2018 | Blakemore et al. |
| 2018/0110544 A1 | 4/2018 | Simpson et al. |
| 2018/0110546 A1 | 4/2018 | Sournac et al. |
| 2018/0132909 A1* | 5/2018 | Hackathorn ....... A61B 17/7065 |
| 2018/0161069 A1 | 6/2018 | DiPaola |
| 2018/0161073 A1* | 6/2018 | Lee .................... A61B 17/7034 |
| 2019/0029734 A1 | 1/2019 | Mickiewicz et al. |
| 2019/0175223 A1 | 6/2019 | Nguyen et al. |
| 2019/0290329 A1 | 9/2019 | Bess et al. |
| 2020/0000505 A1 | 1/2020 | Vitale et al. |
| 2020/0078055 A1 | 3/2020 | Deneuvillers et al. |
| 2020/0237411 A1 | 7/2020 | Jacobs et al. |

OTHER PUBLICATIONS

International Search Report and Written Opinion received for PCT Application No. PCT/IB2020/050707, dated Jul. 31, 2020, 18 pages.

U.S. Appl. No. 16/262,549, filed Jan. 30, 2019, Surgical Device for Spinal Fixation.

* cited by examiner

SURGICAL DEVICE FOR SPINAL FIXATION

CROSS-REFERENCE TO RELATED APPLICATIONS

This application is a continuation application of U.S. application Ser. No. 16/262,549 issued on U.S. Pat. No. 10,869,696 filed on Jan. 30, 2019, entitled "Surgical Device for Spinal Fixation," which is hereby incorporated by reference in its entirety.

FIELD

Surgical devices, systems, and methods for spinal fixation are provided herein.

BACKGROUND

Various fixation devices are commonly used in surgery to align and/or fix a desired relationship between various bone structures within a patient. For example, spinal fixation devices are used in orthopedic surgery to achieve a desired relationship between adjacent vertebral bodies. Such fixation devices typically include one or more spinal fixation elements, such as fixation rods, that can be coupled to adjacent vertebrae by attachment to various bone anchoring devices, such as hooks, bolts, wires, screws, and the like that are embedded in vertebral bodies. In some instances, closure elements, such as screws or nuts, can be used to couple fixation devices to various bone anchoring devices.

However, the anchor assemblies are often secured to bone through penetration of the bone, such as by screws, bolts, and the like. Bone penetration can be detrimental to the patient. For example, it can cause infection, screw breakage, screw misplacement, subsidence, bone fracture propagation, and other complications.

Thus, there remains a need for surgical instruments, methods, and systems for securing spinal fixation elements to bone.

Accordingly, a spinal fixation system is provided herein that is configured to be secured to bony anatomy, for example a spinal fixation system that can be secured without the need to penetrate bone.

SUMMARY

Surgical instruments, methods, and systems are provided for securing spinal fixation elements to bone. In a first aspect, a spinal fixation system is provided that includes a receiver configured to receive at least one fixation member. The receiver has a first end defined by opposed arms with a channel therebetween that is configured to receive the at least one fixation member and a second end that is operably coupled to a hook member. The hook member has an open portion that is configured to engage a portion of bone. A cable is attachable to the receiver, and it is configured to encircle the bone to extend across the open portion to secure the receiver to the bone without penetrating the bone. A closure member is insertable between the opposed arms of the receiver, and it is configured to compress the fixation member into the receiver.

The spinal fixation system can have a number of variations. For example, the hook member can have a distal-most blade portion that forms an edge of the open portion, the blade portion can have a channel therethrough to receive a first end of the cable. In another example, the cable is pre-curved such that the cable is configured to be passed around lamina. The receiver can also have at least first and second receiving members thereon that are configured to receive corresponding first and second ends of the cable, and the first and second ends of the cable can be configured to be crimped to secure them in the first and second receiving members. In another example, each of the opposed arms can have a loop thereon that is configured to receive an end of the cable therethrough. In some examples, the at least one fixation member can include a spinal rod, and the closure member can include a set screw.

In another aspect, a spinal fixation system is provided that has a receiver configured to receive at least one fixation member. The receiver can have a first end defined by opposed arms with a channel therebetween that is configured to receive the at least one fixation member and a second end. A hook member is operably coupled to the second end of the receiver, and the hook member has an open portion that is configured to engage a portion of bone to secure the receiver to the bone without penetrating the bone. The hook member can be configured to move relative to the receiver from an open position allowing release of the bone to a closed position securely gripping the bone when the bone is received in the open portion. The system also has a closure member insertable between the opposed arms of the receiver, and it is configured to compress the fixation member into the receiver.

The spinal fixation system can have a number of variations. For example, the hook member can operably couple to the receiver through a threaded shaft, and the hook member can be configured to move relative to the receiver from the open position to the closed position through rotation of the threaded shaft. The spinal fixation system can also include a cam mechanism that is configured to move the hook member relative to the receiver from the open position to the closed position. In another example, the cam mechanism can have an arm configured to cause actuation of the cam mechanism when the arm is pivoted from a proximal position to a distal position. In one example, the spinal fixation system can also include a cam lock that is configured to prevent release of the cam mechanism after the cam mechanism has moved the hook member to the closed position. In some examples, the cam lock can be configured to prevent release of the cam mechanism when the cam lock contacts the fixation member received in the receiver. The spinal fixation system can also include a ratchet mechanism configured to move the hook member relative to the receiver from the open position to the closed position. In one example, the ratchet mechanism can include an arm and a spring, and the arm can be configured to pivot from a disengaged position in which the hook member is in the open position to an engaged position in which the hook is in the closed position. The spring is configured to resist movement of the arm. In another example, the hook member can have a bone-engaging surface that faces the open position of the hook member that is rougher than a non-bone engaging surface thereof. The bone-engaging surface can be configured to grip the bone received thereagainst.

In another aspect, a spinal fixation method is provided that includes inserting bone into an open portion of a hook member on a distal end of a receiver. The method also includes encircling the bone with a cable attached to the receiver to secure the hook member to the bone without penetrating the bone such that the cable extends across the open portion. The method also includes inserting a spinal rod into a channel defined by opposed arms on a proximal end of the receiver of the surgical device, and rotating a set screw between the opposed arms to secure the spinal rod into the channel.

The method can have numerous variations. For example, the method can also include passing first and second ends of the cable through receiving members on the receiver. In another example, the method can include, after passing the first and second ends through the receiving members, crimping each of the first and second ends to secure the cable to the receiver and the receiver to the bone. The method can also include passing the first end of the cable through a channel formed in a distal-most blade portion of the hook member, and the channel can be one of the receiving members. In some examples, the cable can be a pre-curved cable, and encircling the bone with the cable can include passing the cable through a first secure engagement on a distal end of the hook member, beneath and around the bone, along a posterior of a spine of a patient, and through a second secure engagement on the receiver.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1A:
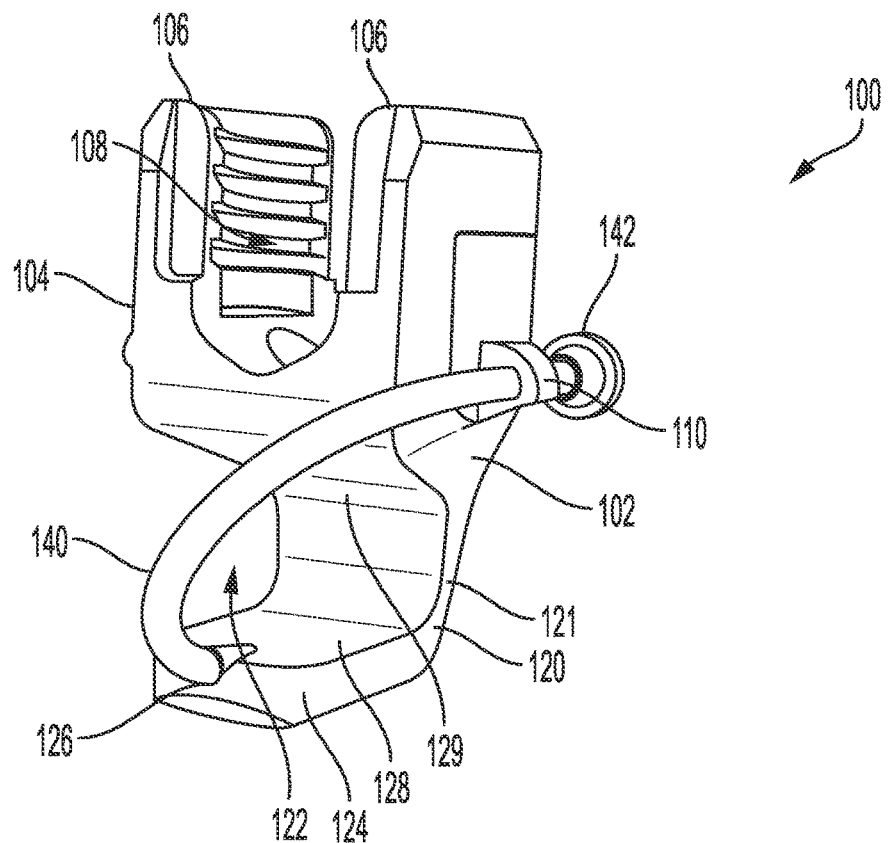
FIG. 1A is a perspective view of one embodiment of a spinal fixation system component.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, devices, and systems are provided for securing a fixation system to one or more portions of spinal anatomy, such as lamina, in a patient without penetrating the spinal anatomy. Spinal fixation devices that are used in spinal and orthopedic surgery typically include one or more spinal fixation elements, such as fixation rods, that can be coupled to adjacent vertebrae by as a result of being attached and secured within various anchor assemblies. The anchor assemblies can include screws, bolts, and the like that can be secured to the spinal fixation elements through the use of various implants, securing means, or fastening members, such as nuts. The anchor assemblies are often secured to spinal anatomy through penetration of the spinal anatomy, such as by the screws, bolts, and the like. Being secured through penetration can provide strong fixation between the anchor assemblies and the spinal anatomy. However, in some cases, this penetration can potentially weaken the spinal anatomy or cause infection, screw breakage, screw misplacement, and other complications for the patient and the surgeon. Accordingly, spinal fixation systems are provided herein that are configured to be secured to spinal anatomy, and some of the systems are configured to be secured without penetrating the spinal anatomy.

An exemplary spinal fixation system has a receiver with proximal and distal ends. The proximal end of the receiver is configured to receive various fixation members, such as spinal rods and set screws, therein. The distal end of the receiver has a hook member that is operably coupled thereto and that is configured to define an opening that is configured to receive a portion of a spinal anatomy, such as lamina, various other elements on a vertebra or a patient's vertebrate spinal column, etc., therein. The hook member is configured to be secured to the spinal anatomy without penetrating the spinal anatomy through a variety of means, as discussed below.

FIGS. 1A-1E illustrate one embodiment of a spinal fixation system 100 that has a cable 140 that is configured to assist in securing the spinal fixation system 100 to a portion of a spinal anatomy, such as lamina. The spinal fixation system 100 has a receiver 102 with a receiver head 104 and a hook member 120, and the hook member 120 extends distally from the receiver head 104 and defines an opening 122 that is configured to receive the portion of spinal anatomy in an open portion thereof. The cable 140 is configured to extend across the opening 122 such that, when the portion of spinal anatomy is received in the opening 122, the cable 140 is configured to be tightened across the opening 122 and secure the hook member 120 to the spinal anatomy without penetrating the spinal anatomy.

In the exemplary embodiment shown in FIGS. 1A-1E, the receiver head 104 is configured to receive various spinal fixation members, such as a spinal rod, and is integrally formed with the hook member 120. Accordingly, the receiver head 104 has opposed arms 106 at a proximal end thereof with a channel 108 between the arms 106 that is configured to receive the spinal fixation members. The opposed arms 106 have threading on surfaces facing the channel 108 that is configured to engage with various closure members, such as a set screw, after a spinal fixation member is received therein. The receiver head 104 also has at least one cable engagement mechanism thereon that is configured to receive at least one end of the cable 140. As illustrated in FIGS. 1A-1E, the engagement mechanism is in the form of loops 110 on opposed sides of the receiver head 104. However, the engagement mechanism on the receiver head 104 can take a variety of other forms, such as various loops, pins, closures, hooks, etc.

As noted above, the hook member 120 is of a shape that defines an opening that is configured to receive a portion of spinal anatomy, such as lamina, therein. The hook member 120 includes a hook arm 121 that extends distally from the receiver head 104 and a blade 124 at a distal end of the hook arm that extends at an angle α relative to the hook arm to form one edge of the opening 122. The blade 124 can be oriented relative to the hook arm 121 at any suitable angle. An angle of approximately 90 degrees is shown in FIGS. 1A-1E, however a person skilled in the art will appreciate that the angle α can be anywhere in the range from about 45 degrees to about 130 degrees. In the embodiment of FIGS. 1A-1E, the hook member 120 is integral with the receiver head 104, however one skilled in the art will appreciate that the hook member 120 can be formed separately from the receiver head 104. The blade 124 also has a bone-engaging surface 128 that faces spinal anatomy to be received in the opening 122. Although the bone-engaging surface 128 and a bone-engaging surface 129 that is opposing the bone-engaging surface 128 across the opening 122 shown in FIGS. 1A-1E are smooth, the bone-engaging surfaces can include a roughened surface portion to enhance bone-gripping ability to increase static and dynamic friction between the spinal anatomy and the hook member to prevent slipping once the hook member is implanted. For example, the bone-engaging surfaces can be grit-blasted.

The hook member 120 has at least one cable engagement mechanism thereon that is configured to receive at least one end of the cable 140. As illustrated in FIGS. 1A-1E, the engagement mechanism is in the form of a channel 126 that extends from a front face of the blade 124 to a back face thereof. However, the engagement mechanism is not limited thereto and can take the form of various loops, pins, closures, hooks, etc.

The cable 140 is configured to secure the hook member 120 to spinal anatomy by closing the opening 122 when spinal anatomy is received therein and the cable is tightened. As illustrated, one end of the cable 140 can be received in the at least one cable engagement mechanism on the receiver head 104 and the at least one cable engagement mechanism on the hook member 120. For example, as illustrated in FIGS. 1A-1E, the cable 104 has first and second ends 142, 144 that are received in one of the loops 110 formed on the receiver head 104 and the channel 126 of the blade 124 in the hook member 120. However, the cable 140 can engage with various mechanisms on the receiver 102 to close the opening 122. The first and second ends 142, 144 are crimped close after passing through the loop 110 and the channel 126 and the cable 140 is tightened. As illustrated, the first and second ends of the cable can be enlarged with respect to the body of the cable, or the cable may include terminal caps. It is to be understood that a variety of securing means can be used, such as adhesives, welding, clips, etc. In various embodiments, the cable can be pre-curved to assist with placement, such as assisting with insertion below bony anatomy, and/or to curve the cable away from various parts of a patient's body. For example, the cable can be curved posteriorly away from neural elements, including the spinal cord.

Figure 1B:
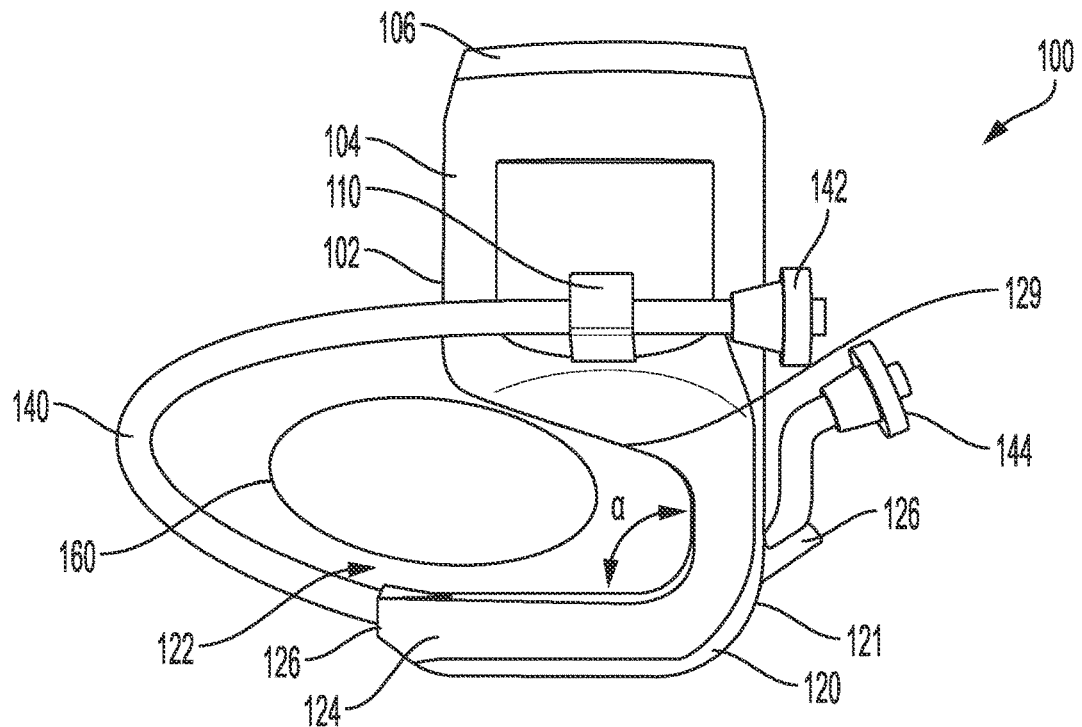
FIG. 1B is a side view of the spinal fixation system component of FIG. 1A secured to a portion of a lamina.
Figure 1C:
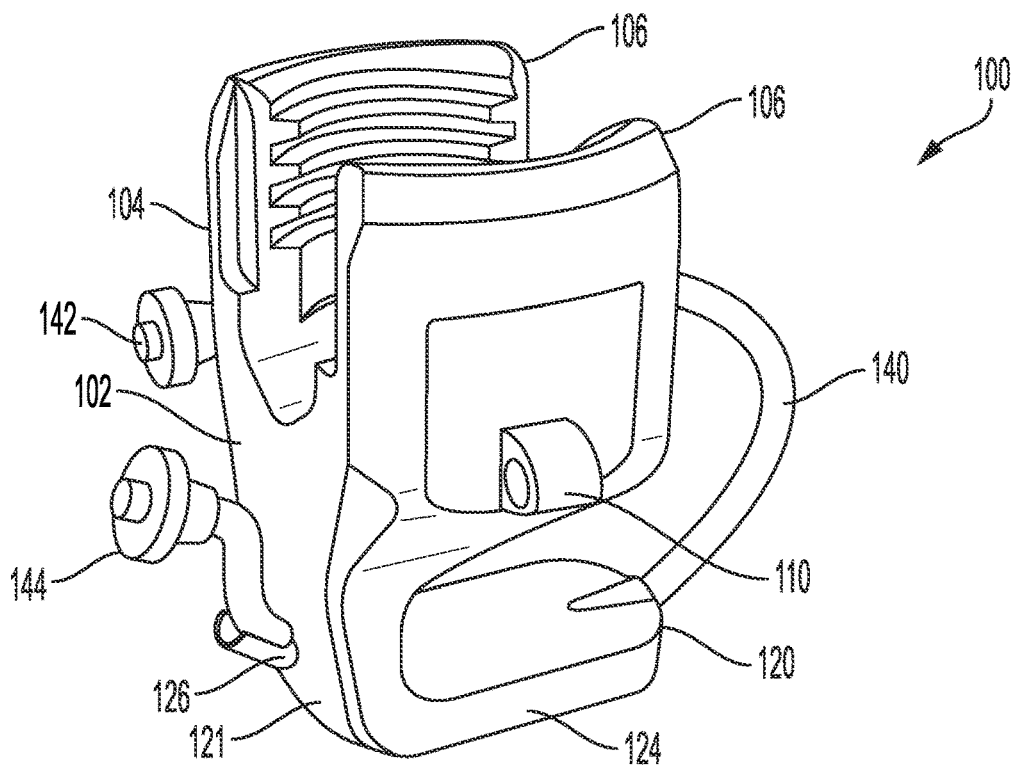
FIG. 1C is a perspective view of the spinal fixation system component of FIG. 1A.
Figure 1D:
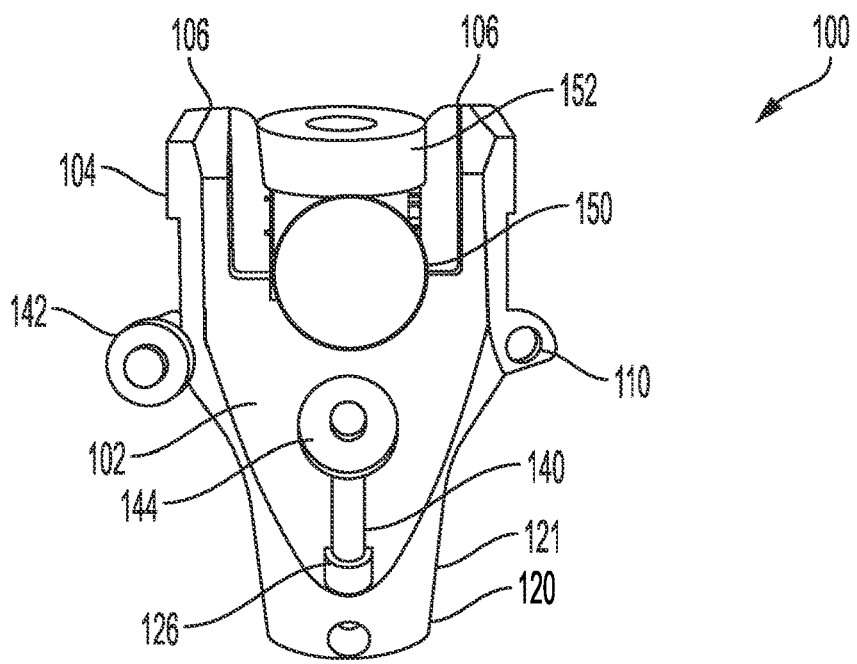
FIG. 1D is a back view of the spinal fixation system component of FIG. 1A with a spinal rod and a set screw.
Figure 1E:
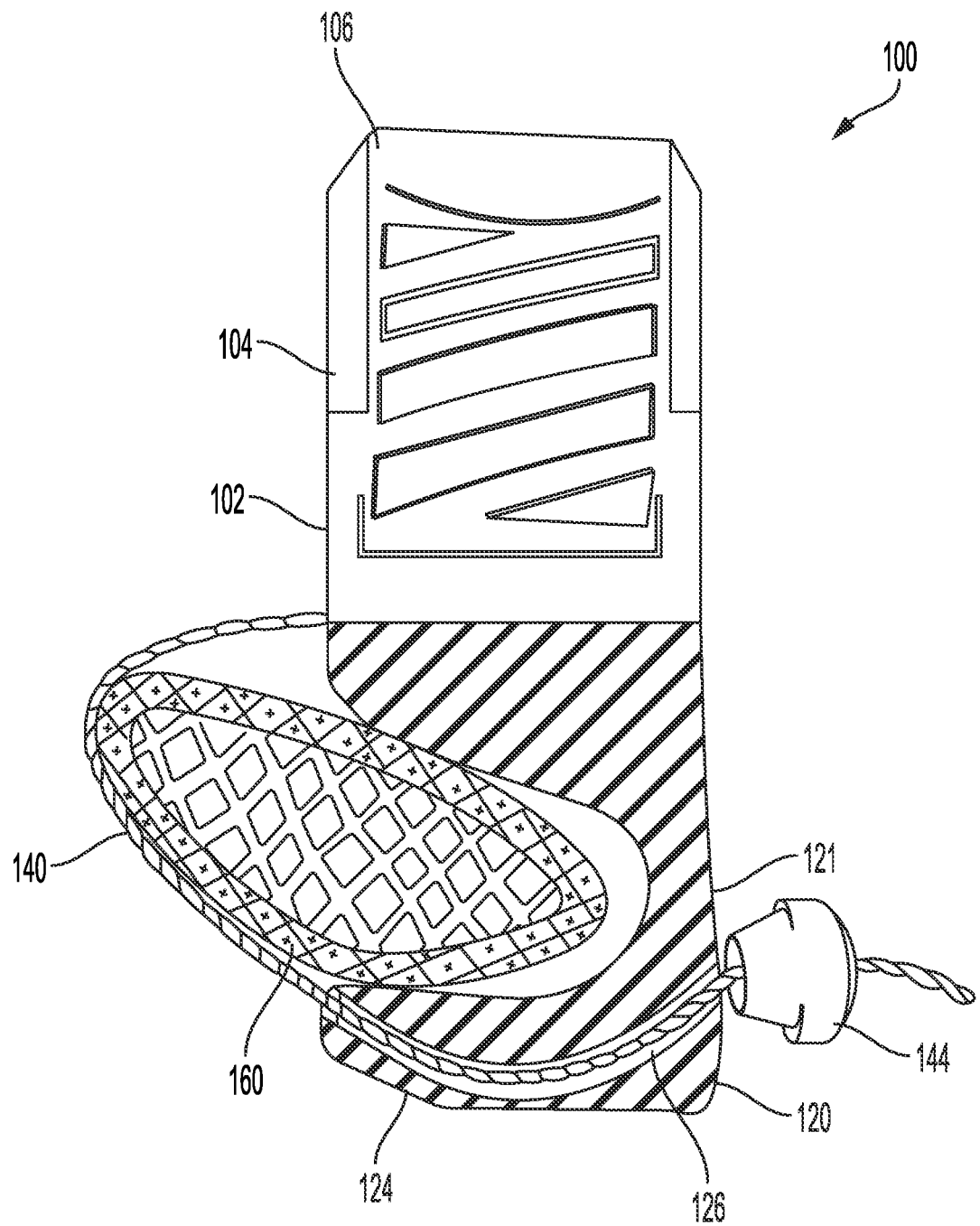
FIG. 1E is a cross-sectional side view of the spinal fixation system component of FIG. 1A secured to a portion of a lamina.

In use, the spinal fixation system 100 is inserted into a body of a patient. A selected portion of the spinal anatomy, such as a portion of a lamina 160 illustrated in FIG. 1B, is inserted into the opening 122 of the hook member 120. The cable 140 is wrapped around the spinal anatomy, and each of the first and second ends 142, 144 are secured to the receiver 102 after pulling the cable 140 tight across the opening 122 and into securing engagement with the spinal anatomy. The first and second ends 142, 144 are passed through the loop 110 and the channel 126 and crimped on the other side to keep the cable 140 secured in place with respect to the receiver 102 and the spinal anatomy. While the cable 140 is only passed around spinal anatomy once in the illustrated embodiment, the cable 140 can be passed around spinal anatomy and through the receiver 102 multiple times if needed, especially to distribute any load placed on the spinal anatomy. A spinal fixation member, such as a spinal rod 150 as illustrated in FIG. 1D, is inserted into the channel 108 and a closure member, such as a set screw 152 as illustrated in FIG. 1D, is threaded between the opposed arms 106. The closure member is then rotated into a secured engagement with the fixation member secure the fixation member with respect to the receiver 102 and the closure member. In an embodiment with a pre-curved cable, a selected portion of the spinal anatomy, such as a portion of lamina, is still inserted into the hook member. The cable is then introduced by threading it through the channel of the blade, underneath the lamina, and out of the spinal canal between adjacent level laminae. The cable is then passed through the upper loop on the receiver head, where the cable is crimped.

Figure 2A:
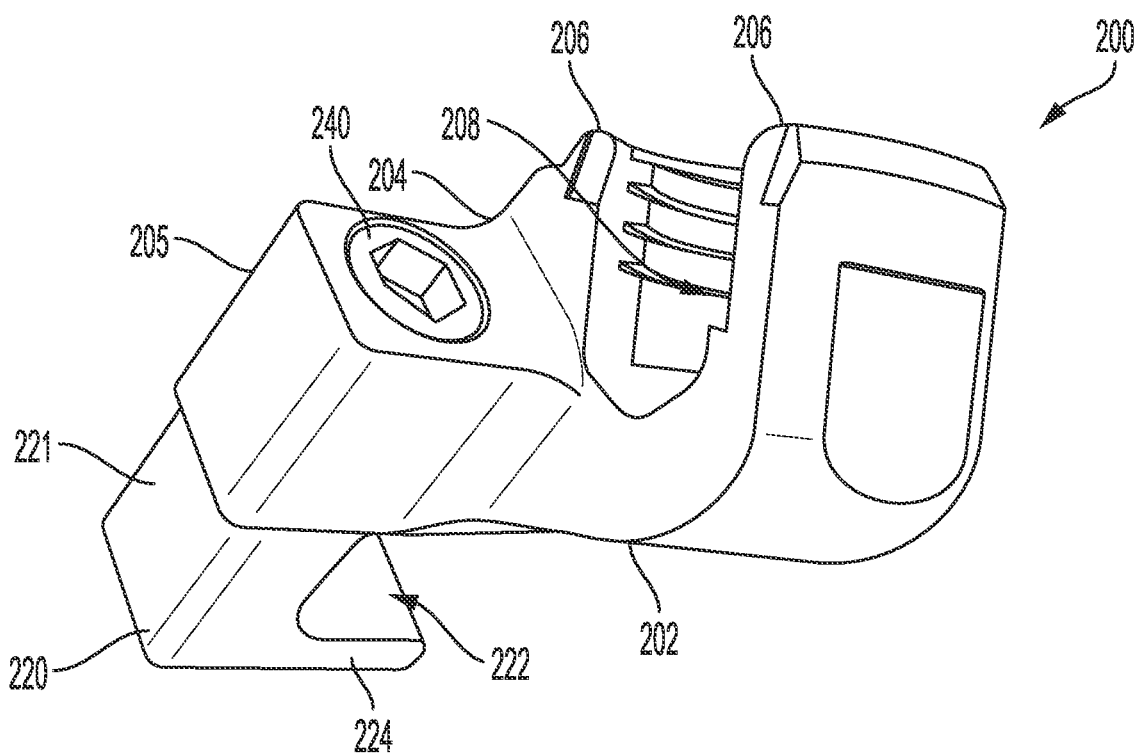
FIG. 2A is a perspective view of another embodiment of a spinal fixation system component.
Figure 2B:
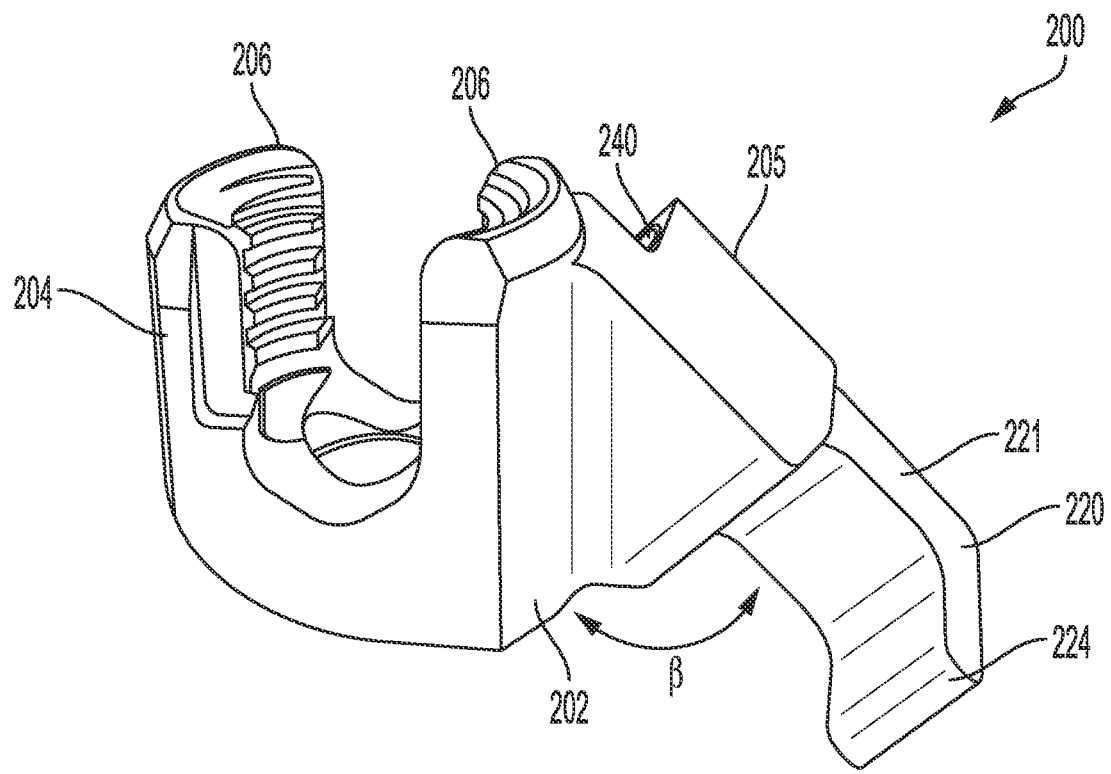
FIG. 2B is a perspective view of the spinal fixation system component of FIG. 2A.
Figure 2C:
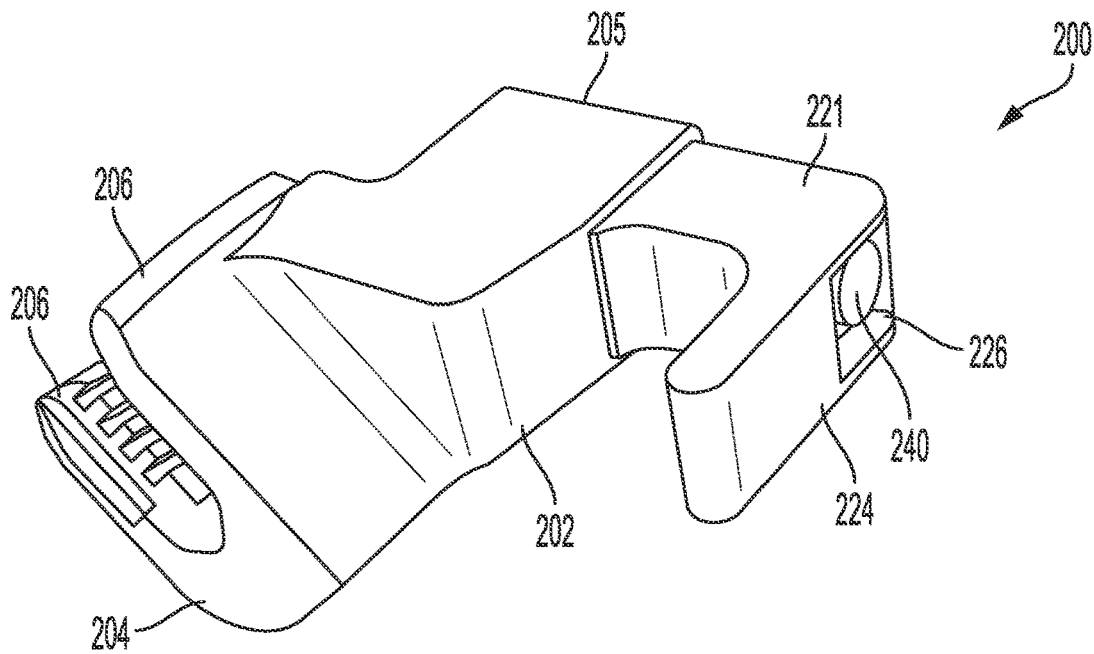
FIG. 2C is a perspective view of the spinal fixation system component of FIG. 2A.

While in the embodiment of FIGS. 1A-1E, the receiver head 104 and the hook member 120 are immovable relative to each other, the hook member can be configured to move relative to the receiver head in other embodiments. For example, FIGS. 2A-2C illustrate another embodiment of a spinal fixation system 200 similar to the spinal fixation system 100. However, the spinal fixation system 200 has a hook member 220 that is configured to be movable relative to a receiver head 204 such that movement of the hook member 220 secures the spinal fixation system 200 to a portion of spinal anatomy, such as lamina. The spinal fixation system 200 has a receiver 202 with the receiver head 204 and the hook member 220, and the hook member 220 extends distally from the receiver head 204 and defines an opening 222 that is configured to receive the portion of spinal anatomy in an open portion thereof. The hook member 220 is configured to move proximally toward the receiver head 204 so that, when the spinal anatomy is received in the opening 222, the hook member 220 securely grips the spinal anatomy within the opening 222 between the hook member 220 and the receiver head 204 to secure the receiver 200 to the spinal anatomy without penetrating the spinal anatomy.

In the exemplary embodiment shown in FIGS. 2A-2C, the receiver head 204 is configured to receive various spinal fixation members, such as a spinal rod. Accordingly, it has opposed arms 206 at a proximal end thereof with a channel 208 between the arms 206 that is configured to receive a spinal fixation member. The opposed arms 206 have threading on surfaces facing the channel 208 that is configured to engage with various closure members, such as a set screw, after a spinal fixation member is received therein.

The receiver head 204 is also configured to receive a proximal end of the hook member 220 when the hook member 220 is moved proximally. It thus has a hook engagement portion 205, which can be in the form of a flange, associated therewith. The engagement portion 205 can have a cavity formed therein that is configured to facilitate engagement with a portion of the hook member 220. The cavity of the hook engagement portion 205 has a channel therethrough that is configured to receive a threaded shaft 240, discussed in detail below. The receiver head 204 is angularly offset at an angle β from the hook member 220 while the hook engagement portion 205 is aligned with the hook member 220. The receiver head 204 can be oriented relative to the hook member 220 at any suitable angle. An angle of approximately 45 degrees is shown in FIGS. 2A-2C, however a person skilled in the art will appreciate that the angle β can be anywhere in the range from about 0 degrees to about 90 degrees.

Similar to the hook member 120, the hook member 220 is of a shape that defines an opening that is configured to receive a portion of spinal anatomy, such as lamina, therein. The hook member 220 includes a hook arm 221 that extends distally from the receiver head 204 and a blade 224 at a distal end of the hook arm that extends at an angle relative to the hook arm to define one edge of the opening 222. While the illustrated angle of the blade 224 is approximately 90 degrees, the blade 224 can extend at a variety of angles similar to the angle α, discussed above with respect to FIGS. 1A-1E. The blade 224 has a bone-engaging surface, i.e., defining a portion of opening 222, that securely grips a portion of spinal anatomy, such as lamina, in the opening 222 when the hook member 220 moves proximally into the receiver head 204. While the illustrated bone-engaging surface is smooth, it can be rougher than surrounding surfaces to better grip the spinal anatomy, such as having a textured surface that results from a process such as grit-blasting.

As noted above, the hook member 220 is configured to move proximally into the receiver head 204 to engage with and close onto spinal anatomy received in the opening 222, and it is not integral with the receiver head 204 so as to allow relative movement between the hook member and the receiver head. The hook member 220 has a channel 226 defined therein that is axially aligned with the channel of the hook engagement portion 205 and is also configured to receive the threaded shaft 240 therein. An inner surface of the channel 226 is at least partially threaded to engage with corresponding threads on the threaded shaft 240, and the hook member 220 is configured to move proximally and distally with respect to the receiver head 204 upon rotation of the threaded shaft 240 in one direction or the other. While the inner surface of the channel 226 has threading thereon, one skilled in the art will understand that various threaded components can be added to the channel 226, such as nuts, to provide a corresponding threading to engage the threaded shaft 240 while maintaining a smooth inner surface.

As noted, the threaded shaft 240 is configured to cause relative movement between the hook member 220 and the receiver head 204, and it thus has a drivable head that rests against a surface of the hook engagement portion and an elongate, threaded body that extends through the channels of the receiver head 204 and the hook member 220. Upon a driver tool being used to rotate the head of the threaded shaft 240, the threaded body is configured to rotate and cause the relative movement between the receiver head 204 and the hook member 220 in either proximal or distal direction, depending on the direction of rotation. In some embodiments, the threaded shaft can have a swage or nut distal end to prevent the hook member and the receiver head from being disengaged from one another.

In use, the spinal fixation system 200 is inserted into a body of a patient. A selected portion of the spinal anatomy, such as the lamina, is inserted into the opening 222 of the hook member 220. A driver tool is used to rotate the threaded shaft 240, which causes the hook member 220 to retract towards the receiver head 204. Threading in the channel 226 of the hook member 220 engages with threading on the threaded shaft 226 to cause the hook member to translate up and down depending on the direction of rotation. As the threaded shaft 226 is rotated, the hook member 220 moves from an open position to a closed position in which spinal anatomy in the opening 222 is secured between the receiver head 204 and the hook member 220. A spinal fixation member, such as a spinal rod, is inserted into the channel 208 and a closure member, such as a set screw, is threaded between the opposed arms 206. When any required spinal adjustments are made, the closure member is then rotated into a secured engagement with the fixation member such that the fixation member cannot move with respect to the receiver 202 or the closure member.

Figure 2D:
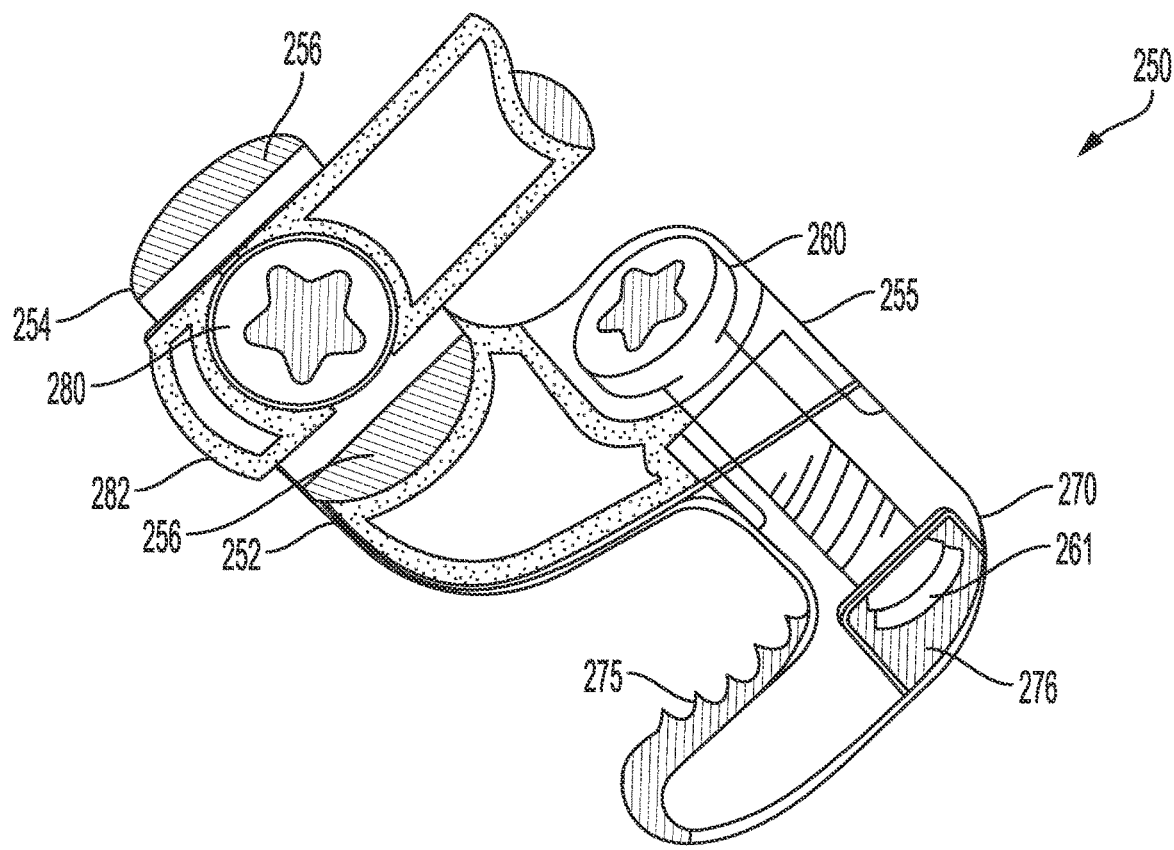
FIG. 2D is a top-down partial cross-sectional view of another embodiment of a spinal fixation system component similar to the spinal fixation system component of FIG. 2A.

FIG. 2D illustrates another embodiment of a spinal fixation system 250 that is similar to the spinal fixation system 200. For example, the spinal fixation system 250 has a hook member 270 that is configured to be movable relative to a receiver head 254 such that movement of the hook member 270 secures the spinal fixation system 250 to a portion of spinal anatomy, such as lamina. The spinal fixation system 250 has a receiver 252 with the receiver head 254 and the hook member 270, and the receiver head 254 is configured to receive various spinal fixation members, such as a spinal rod 282. It has opposed arms 256 at a proximal end thereof that are configured to receive a set screw 280 therebetween. The receiver head 254 has a hook engagement portion 255 with a cavity formed therein that is configured to facilitate engagement with a portion of the hook member 270. The cavity of the hook engagement portion 255 has a channel therethrough that is configured to receive a threaded shaft 260, and the hook member 270 has a channel 276 defined therein that is axially aligned with the channel of the hook engagement portion 255 and is also configured to receive the threaded shaft 260 therein. An inner surface of the channel 276 is at least partially threaded to engage with corresponding threads on the threaded shaft 260, and the hook member 270 is configured to move proximally and distally with respect to the receiver head 254 upon rotation of the threaded shaft 260 in one direction or the other. However, unlike the spinal fixation system 200, the threaded shaft 260 has a swage distal end 261, and a bone-engaging surface 275 is rougher than surrounding surfaces to better grip the spinal anatomy.

Hook members can move relative to receiver heads in a variety of ways other than as described above. For example, FIGS. 3A-3D illustrate another embodiment of a spinal fixation system 300 similar to the spinal fixation system 200. However, the spinal fixation system 300 has a hook member 320 that is configured to be movable relative to a receiver head 304 by a cam mechanism. The spinal fixation system 300 has a receiver 302 with the receiver head 304 and the hook member 320, and the hook member 320 extends distally from the receiver head 304 and defines an opening 322 that is configured to receive spinal anatomy in an open portion thereof. A cam mechanism 340 engages both the receiver head 304 and the hook member 320, and actuation of the cam mechanism 340 is configured to cause proximal movement of the hook member 320 relative to the receiver head 304 to securely grip the spinal anatomy within the opening 322 without penetrating the spinal anatomy.

In the exemplary embodiment shown in FIGS. 3A-3D, the receiver head 304 is configured to receive various spinal fixation members, such as a spinal rod 370. Accordingly, the receiver head has opposed arms 306 on a proximal end thereof with a channel 308 between the arms 306 that is configured to receive a spinal fixation member. The opposed arms 306 have threading on surfaces facing the channel 308 that is configured to engage with various closure members, such as a set screw, after a spinal fixation member is received therein.

The receiver head 304 is also configured to receive a proximal end of the hook member 320 when the hook member 320 is moved proximally. As such, it engages the cam mechanism 340 on a distal portion 310 thereof. A longitudinal opening 360 is defined in a distal portion 310 of the receiver head 304 that is configured to allow a cam bar 350 of the hook member 320, discussed below, to slide therealong during actuation of the cam mechanism 340 and relative movement of the hook member 320.

The hook member 320 is of a similar shape to the hook members described above with respect to FIGS. 1A-1E and 2A-2C in that it defines an opening that is configured to receive a portion of spinal anatomy, such as lamina, therein. The hook member 320 includes a hook arm 321 that extends distally from the receiver head 304 and a blade 324 at a distal end of the hook arm that extends at an angle relative to the hook arm to define one edge of the opening 222. While the illustrated angle of the blade 324 is approximately 90 degrees, the blade 324 can extend at a variety of angles similar to the angle α, discussed above with respect to FIGS. 1A-1E. The blade 324 has a bone-engaging surface that is configured to securely grip spinal anatomy in the opening 322 upon actuation of the cam mechanism 340. While the illustrated bone-engaging surface is smooth, it can be rougher than surrounding surfaces to better grip the spinal anatomy, such as having a textured surface that results from a process such as grit-blasting.

As noted, the hook member 320 is configured to move proximally into the receiver head 304 upon actuation of the cam mechanism 340, and it is not integral with the receiver head 304 so as to allow relative movement between the hook member and the receiver head. The hook arm 321 terminates in the cam bar 350, which slides along the longitudinal opening 360 of the receiver head 304. The cam bar 350 is configured to engage the cam mechanism 340 and move proximally upon actuation thereof, causing the hook member 320 to move proximally with movement of the cam bar 350.

The cam mechanism 340 is thus configured to cause relative movement between the hook member 320 and the receiver head 304 upon its actuation. As such, the cam mechanism 340 has wings 342 disposed on opposite sides of the distal portion 310 of the receiver head 304, and each wing 342 has a plurality of teeth or grooves formed thereon. The grooves are configured to receive the cam bar 350 of the hook member 320 thereon, and they are angled to allow the cam bar 350 to only move proximally along the wings 342 during actuation of the cam mechanism 340. The cam mechanism 340 has an actuation bar 344 that extends behind the receiver head 304 and connects the two wings 342. Each wing 342 is pivotably coupled to opposite distal surfaces of the receiver head 304 such that movement of the actuation bar 344 causes corresponding rotation of the wings 342 about pivot points 340p.

Figure 3A:
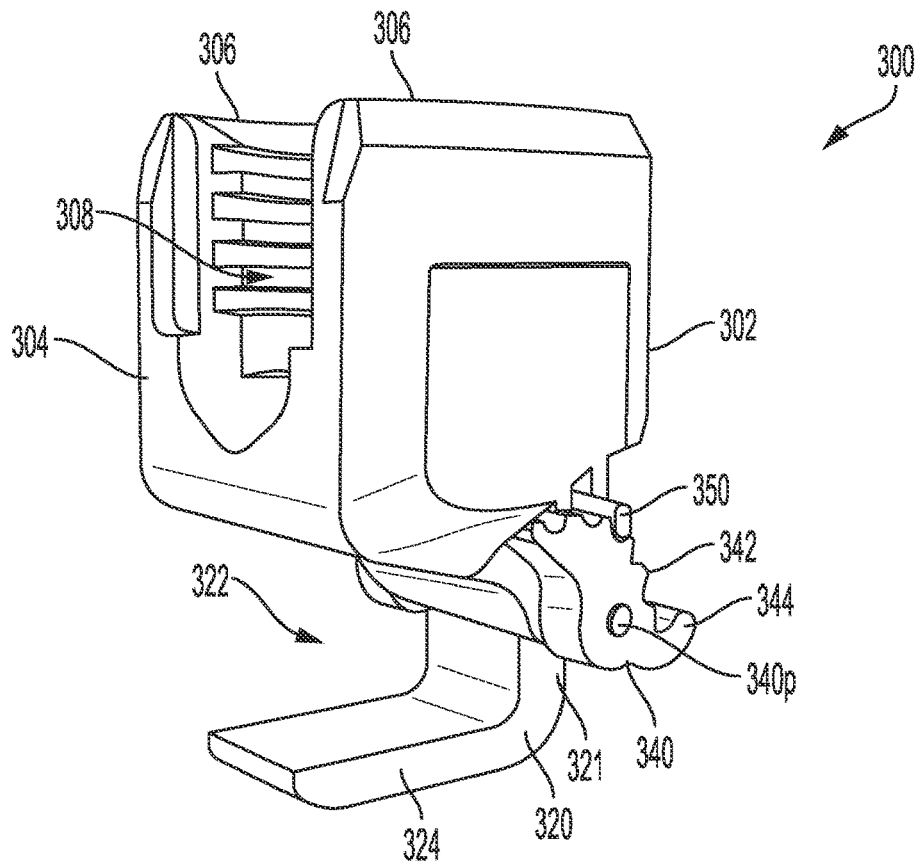
FIG. 3A is a perspective view of another embodiment of a spinal fixation system component.
Figure 3B:
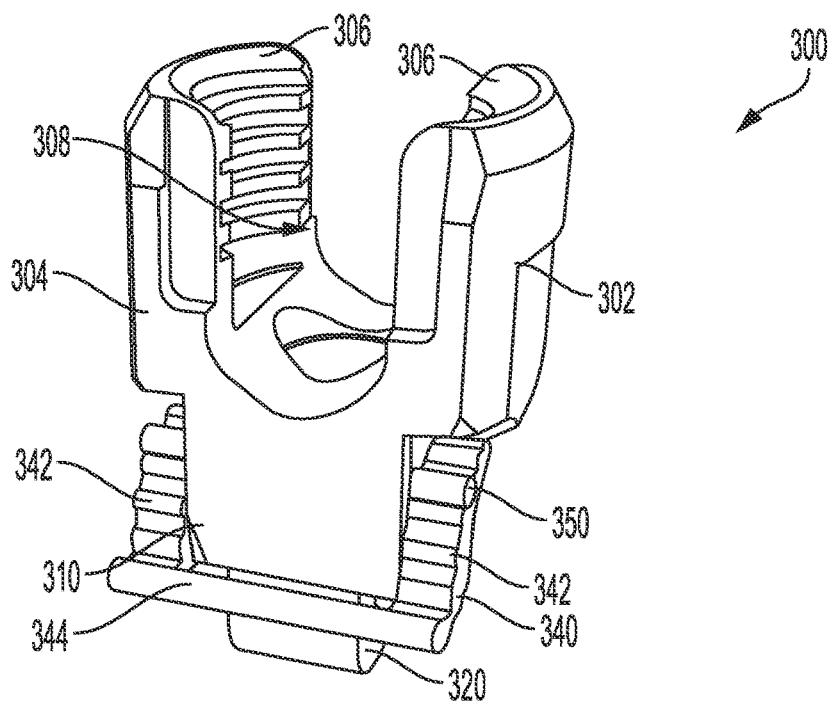
FIG. 3B is a perspective view of the spinal fixation system component of FIG. 3A.
Figure 3C:
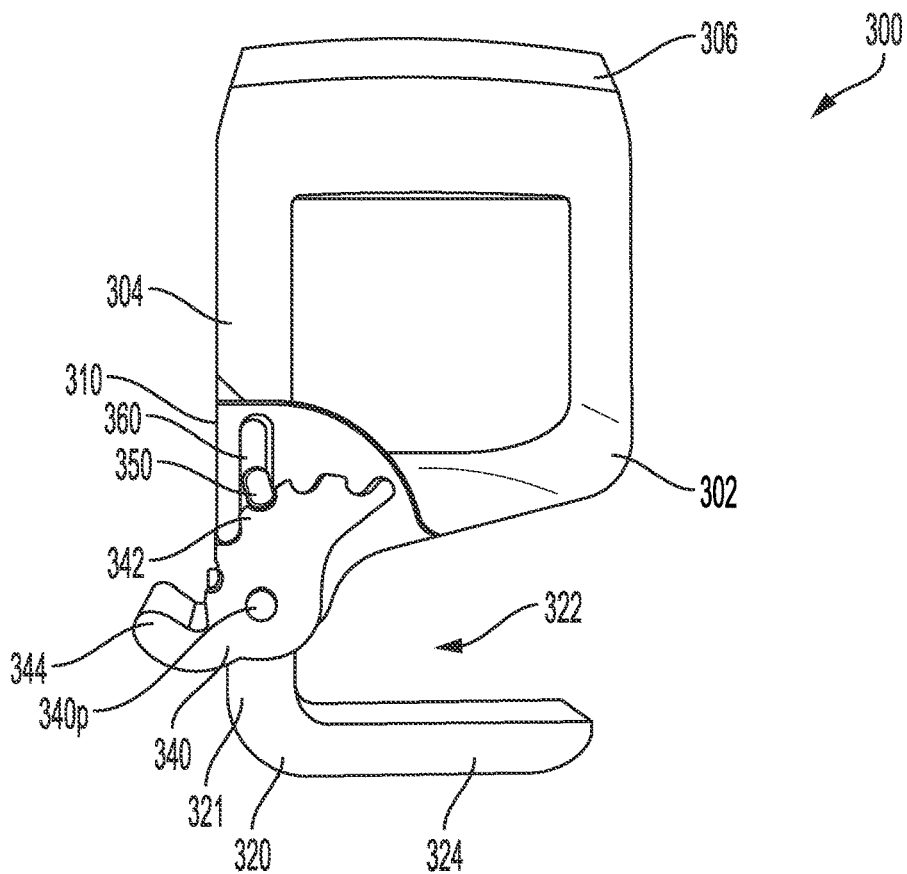
FIG. 3C is a side view of the spinal fixation system component of FIG. 3A.
Figure 3D:
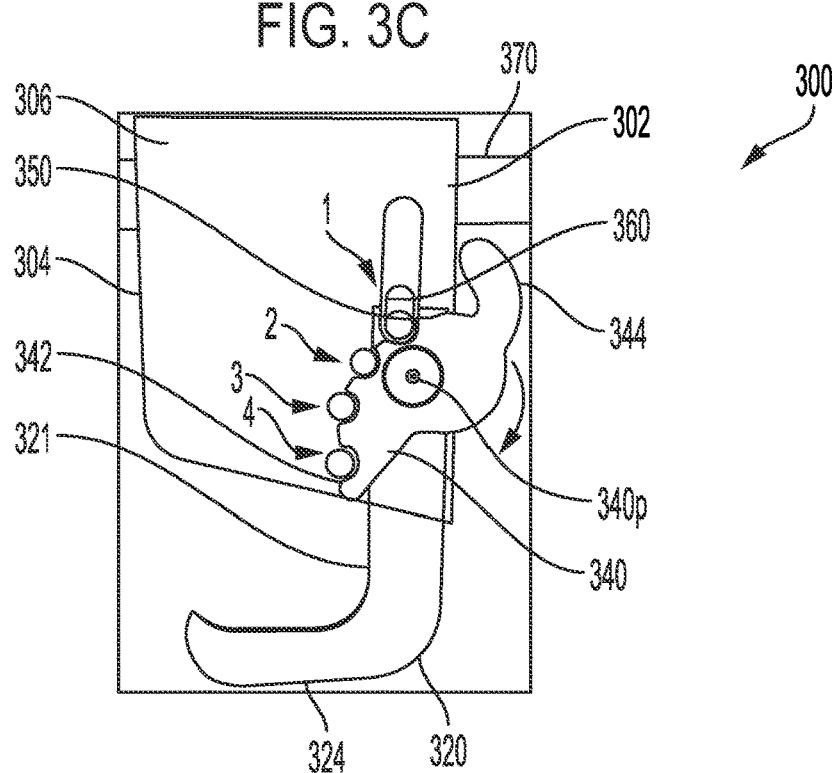
FIG. 3D is a side view of the spinal fixation system component of FIG. 3A attached to a spinal rod.

In use, the spinal fixation system 300 is used similar to the system 200. However, when a selected portion of the spinal anatomy, such as the lamina, is first inserted into the opening 322 of the hook member 320, the cam mechanism is initially in a non-actuated position with the hook member 320 at a distal-most, open positon relative to the receiver head 304, as illustrated in FIG. 3D. The cam bar 350 is initially positioned distally in the longitudinal opening 360 of the receiver head 304 and rests in corresponding groves on each of the wings 342, as noted in FIG. 3D at Position 1. Once the receiver 302 is in position on the spinal anatomy, force is applied to the actuation bar 344 distally through use of a tool, such as a cervical compressor instrument, and the actuation bar 344 rotates distally away from the receiver head 304, as illustrated by an arrow in FIG. 3D, causing the wings 342 to rotate in the same direction about the pivot points. As the wings 342 rotate, the angled grooves apply an upward, proximally directed force on the cam bar 350 of the hook member 320 to lift it proximally along the longitudinal opening 360 toward the receiver head 304 such that the cam bar 350 will enter each subsequent groove on the wings 342, as illustrated at Positions 2, 3, and 4 of FIG. 3D. As the actuation bar 344 completes its rotation, the cam mechanism 340 comes to a rest with the cam bar 350 in a proximal position along the longitudinal opening 360, with the result that the hook member 320 has been moved proximally to a closed position with the cam bar 350 to grip spinal anatomy between the hook member 320 and the receiver head 304.

The distance that the cam bar 350 (and thus the hook member 320) is moved by the cam mechanism 340 depends on a size of the spinal anatomy within the opening 322 such that the cam bar 350 might not enter every groove on each wing 342, and the angled grooves assist in maintaining the hook member 320 in the proximal position.

Figure 4A:
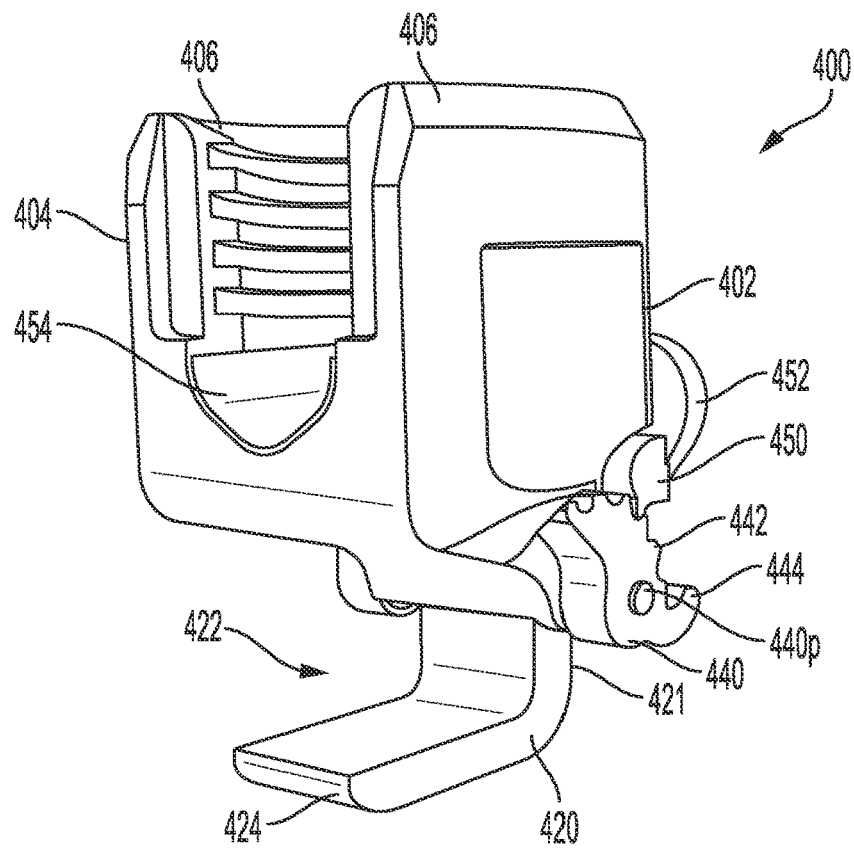
FIG. 4A is a perspective view of another embodiment of a spinal fixation system component.
Figure 4B:
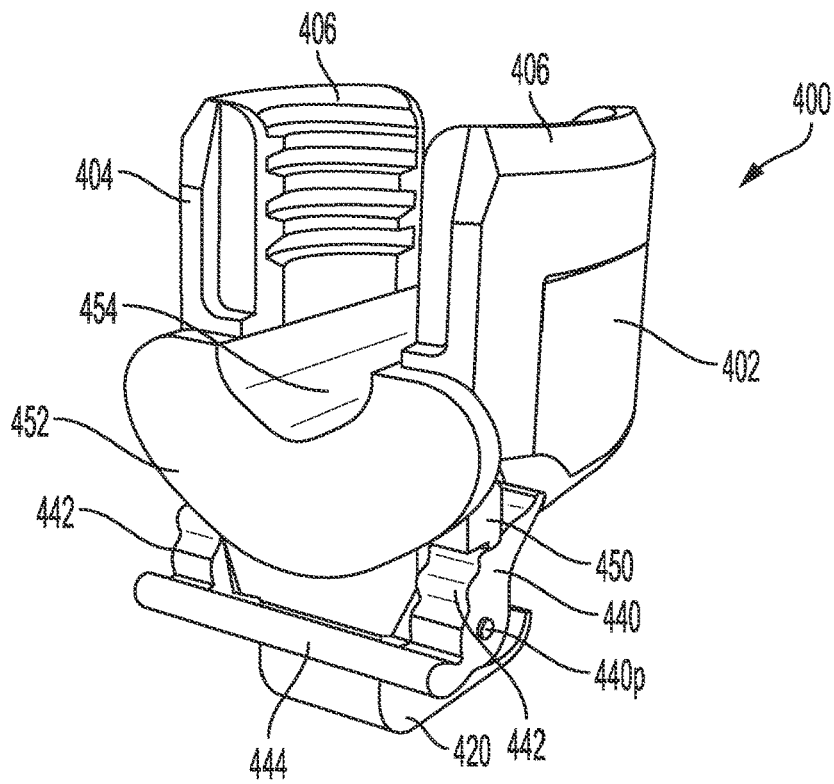
FIG. 4B is a perspective view of the spinal fixation system component of FIG. 4A.
Figures 4C, 5A:
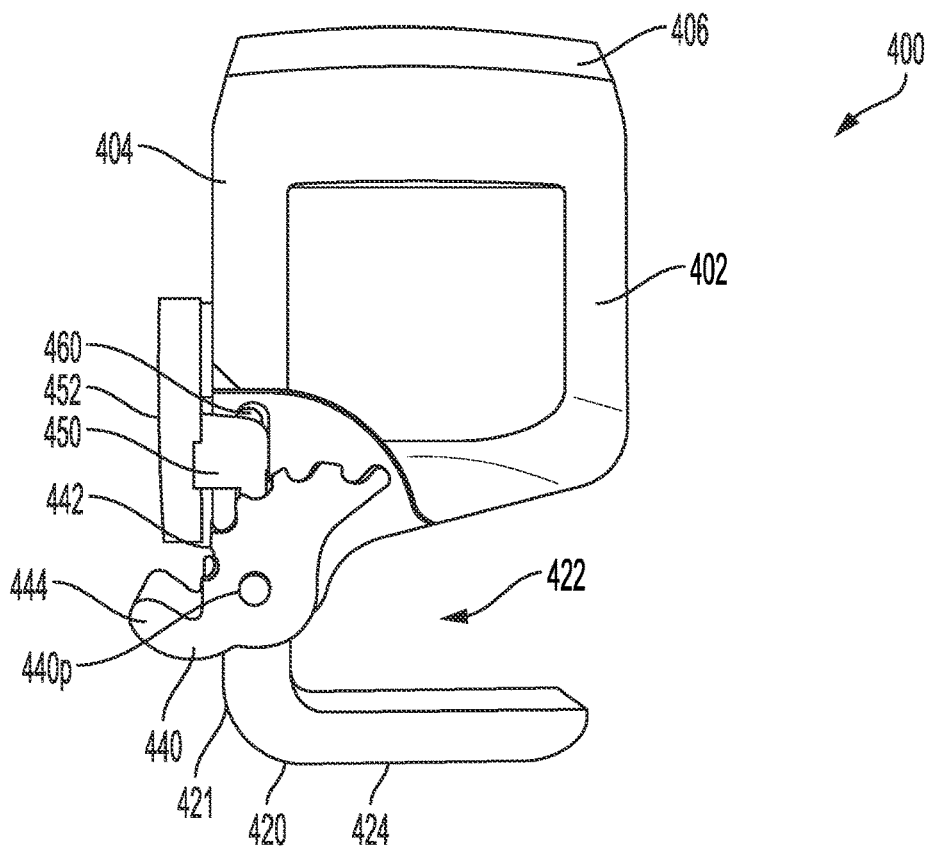
FIG. 4C is a side view of the spinal fixation system component of FIG. 4A.
FIG. 5A is a perspective view of another embodiment of a spinal fixation system component.

Once the cam mechanism has been activated, it can be configured to lock the hook member in the closed position engaged with spinal anatomy during use. As illustrated in FIGS. 4A-4C, another embodiment of a spinal fixation system 400 is provided that is similar to the spinal fixation system 300 with a cam mechanism 340. The spinal fixation system 400 has a receiver 402 with a receiver head 404 and a hook member 420, and the hook member 420 extends distally from the receiver head 404 and defines an opening 422 that is configured to receive a portion of spinal anatomy, such as lamina, in an open portion thereof. A cam mechanism 440 engages both the receiver head 404 and the hook member 420, and actuation of the cam mechanism 440 is configured to cause proximal movement of the hook member 420 relative to the receiver head 404 to securely grip the spinal anatomy within the opening 422 without penetrating the spinal anatomy.

As with the receiver head 304 described above, the receiver head 404 is configured to receive various spinal fixation members, such as a spinal rod. Accordingly, the receiver head has opposed arms 406 on a proximal end thereof with a channel 408 between the arms 406 that is configured to receive a spinal fixation member. The opposed arms 406 have threading on surfaces facing the channel 408 that is configured to engage with various closure members. The receiver head 404 is also configured to receive a proximal end of the hook member 420 when the hook member 420 is moved proximally, and thus it has a longitudinal opening 460 therein that is configured to allow a cam bar 450 of the hook member 420 to slide therealong during actuation.

Similar to the hook member 320, the hook member 420 is configured to move proximally into the receiver head 404 upon actuation of the cam mechanism 440, and it has a blade 424 that can extend at various angles similar to the angle α and a hook arm 421 that terminates in the cam bar 450, which is configured to engage the cam mechanism 440 and move proximally upon actuation thereof. This movement is configured to cause the blade 424 of the hook member 420 to move proximally, as well. While a bone-engaging surface of the blade 424 is smooth, it can be rougher than surrounding surfaces to better grip the spinal anatomy, such as having a textured surface that results from a process such as grit-blasting.

The cam mechanism 440 is similar to the cam mechanism 340 discussed above, as it is configured to cause relative movement between the hook member 420 and the receiver head 404 upon actuation. Wings 442 are disposed on opposite sides of the receiver head 404 and configured to rotate about pivot points 440p, and each wing 442 has angled teeth or grooves formed thereon. An actuation bar 444 extends behind the receiver head 404 and connects the two wings 442.

However, the cam mechanism 440 is configured to lock itself in place, and thus lock the hook member 420 in the closed position. In the illustrated embodiment, the cam mechanism is able to lock itself in place when a spinal fixation member, such as a spinal rod, is received in the receiver head 404. The cam mechanism 440 has a panel 452 that is configured to engage and apply a distally directed force to the cam bar 450. As such it has a saddle 454 integrally formed with the panel 452 that receives a force from the spinal fixation member. The saddle 454 is configured to sit in the channel 408, and the panel 452 extends along a back of the receiver head 404 and rests on top of the cam bar 450. Because of this arrangement, the saddle 454 is configured to be held in place by a spinal fixation member placed on top of the saddle 454 in the channel 408, and the panel 452, in turn, is configured to be held in place by the saddle 454, which subsequently holds the cam bar 450 in place.

During placement, the cam mechanism 440 can be actuated similar to the cam mechanism 340 by applying a distally directed force to the actuation bar 444 by a variety of tools. Thus, the saddle 454 and the panel 452 do not apply sufficient force on the cam bar 450 to prevent movement. However, once the receiver 402 has been placed and the hook member 420 has engaged the spinal anatomy, a spinal fixation member is attached to the receiver 402 and subsequently prevents any proximal movement by the saddle 454 and the panel 452, which keeps the cam bar 450 locked to prevent it from being released until the spinal fixation member has been removed.

FIGS. 5A-5D illustrate another embodiment of a spinal fixation system 500 similar to the spinal fixation system 300. However, the spinal fixation system 500 has a hook member 520 that is configured to be movable relative to a receiver head 504 by a ratchet mechanism. The spinal fixation system 500 has a receiver 502 with the receiver head 504 and the hook member 520, and the hook member 520 extends distally from the receiver head 504 and defines an opening 522 that is configured to receive a portion of spinal anatomy, such as lamina, in an open portion thereof. A ratchet mechanism 540 engages both the receiver head 504 and the hook member 520, and actuation of the ratchet mechanism 540 is configured to cause proximal movement of the hook member 520 relative to the receiver head 504 to securely grip the spinal anatomy within the opening 522 without penetrating the spinal anatomy.

Similar to the receiver head 304, the receiver head 504 is configured to receive various spinal fixation members, such as a spinal rod, therein. Accordingly, it also has opposed arms 506 on a proximal end thereof with a channel 508 between the arms 506 that is configured to receive a spinal fixation member, similar to the other embodiments discussed above. The opposed arms 506 have threading on surfaces facing the channel 508 that is configured to engage with various closure members.

The receiver head 504 is also configured to receive a proximal end of the hook member 520 when the hook member 520 is moved proximally. The receiver head 504 has a longitudinal opening 560 in a distal portion 510 thereof, which is configured to allow ratchet pins 526 of the hook member 520 to slide therealong, as discussed below. Angled teeth 510t extend from a surface of the distal portion 510 that is configured to engage corresponding angled teeth 521t of a hook arm 521 of the hook member 520, as discussed below.

The hook member 520 is of a similar shape as discussed above that defines an opening that is configured to receive spinal anatomy therein. The hook member 520 includes the hook arm 521 that extends distally from the receiver head 504 and a blade 524 at a distal end of the hook arm that extends at an angle relative to the hook arm to define one edge of the opening 522. While the illustrated angle of the blade 524 is approximately 90 degrees, it can extend at a variety of angles similar to the angle α discussed above with respect to FIGS. 1A-1E. The blade 524 has a bone-engaging surface that is configured to securely grip spinal anatomy in the opening 522 upon actuation of the ratchet mechanism 540. While the bone-engaging surface is smooth as illustrated, it can be rougher than surrounding surfaces to better grip the spinal anatomy, such as having a textured surface that results from a process such as grit-blasting.

As noted, the hook member 520 is configured to move proximally into the receiver head 504 upon actuation of the ratchet mechanism 540 due to interaction between the angled teeth 510*t*, 521*t*, as discussed below, and it has ratchet pins 526 that extend therefrom and are configured to slide along the longitudinal opening 560 to guide its movement. The ratchet pins 526 are configured to engage the ratchet mechanism 540 and move proximally upon actuation thereof, causing the hook member 520 and the blade 524 to move proximally with movement of the ratchet pins 526.

Figure 5B:
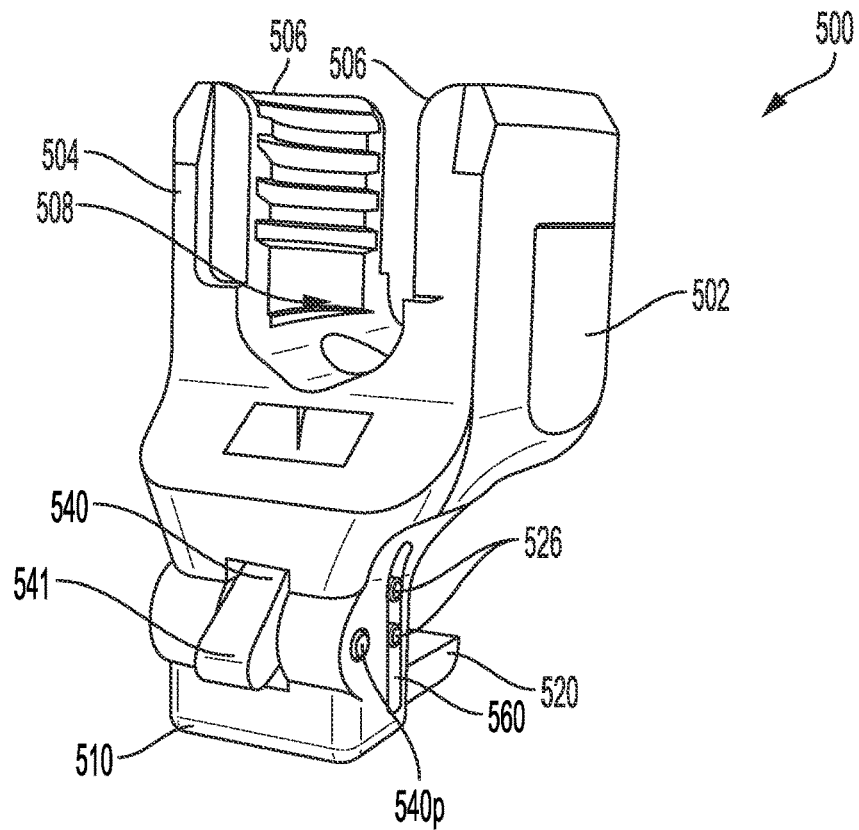
FIG. 5B is a perspective view of the spinal fixation system component of FIG. 5A.
Figure 5C:
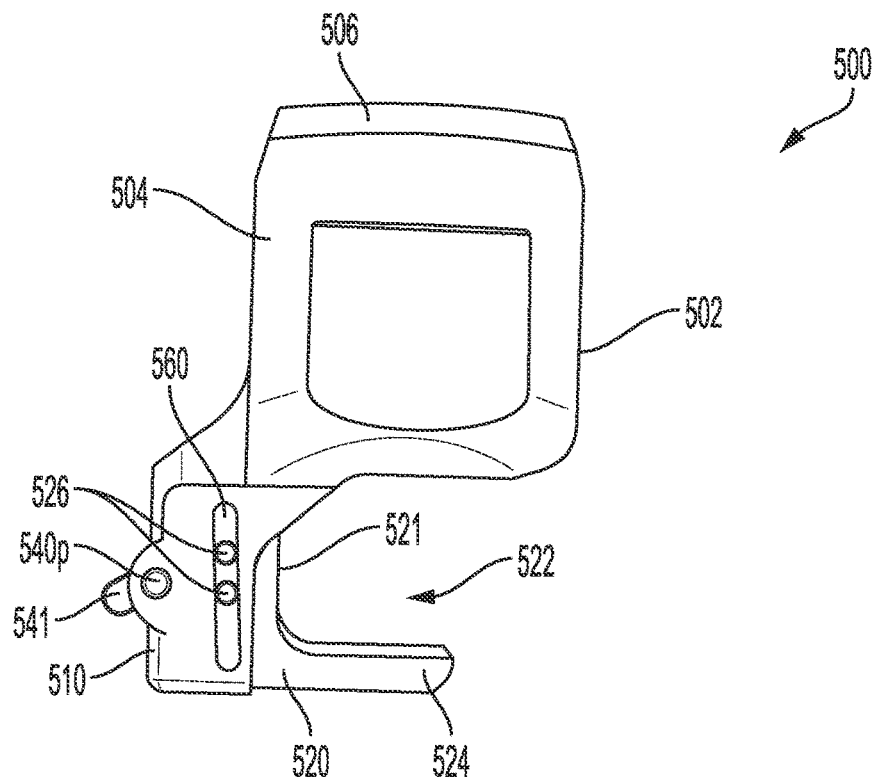
FIG. 5C is a side view of the spinal fixation system component of FIG. 5A.
Figure 5D:
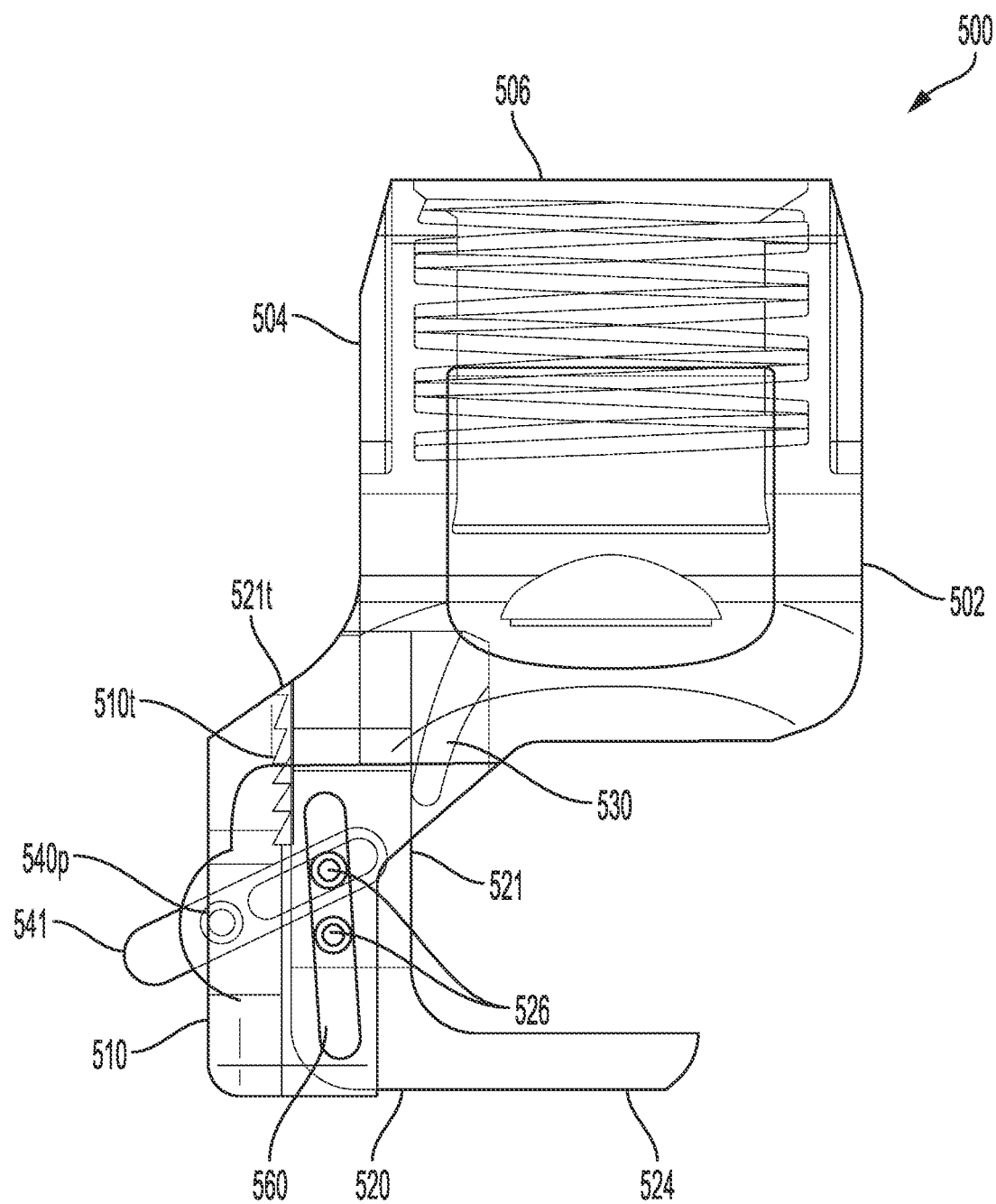
FIG. 5D is a cross-sectional side view of the spinal fixation system component of FIG. 5A.

The ratchet mechanism 540 is consequently configured to cause movement of the hook member 520 toward the receiver head 504 upon actuation. It has a lever 541 protruding from the distal portion 510 of the receiver head 504 that engages with the ratchet pins 526 of the hook member 520 and is configured to rotate about a pivot point 540*p*. As illustrated in FIG. 5D, the angled teeth 510*t*, 521*t* of each of the receiver head 504 and the hook member 520 are held in engagement by a spring 530 extending from the receiver head 540, and the lever 541 is configured to rotate distally about the pivot point 540*p* to force the ratchet pins 526 proximally upon distal actuation of the lever by a tool. The force applied to the lever 540 is configured to cause angled interaction between the angled teeth 510*t*, 521*t* that forces the hook arm 521 to move away from the distal portion 510 of the receiver head 504 and press against the spring 530 until the spring bias is overcome and the angled teeth 510*t*, 521*t* slide past each other as the hook arm 521 moves proximally until the angled teeth 510*t*, 521*t* fall into a new engagement, resulting in distal movement of the hook member 520 and the ratchet mechanism 540 locking in place.

Thus, in use, the ratchet mechanism 540 operates similarly to the cam mechanism 340 by causing the hook member 520 to move proximally toward the receiver head 504 upon distal actuation of the lever 541.

Figure 6A:
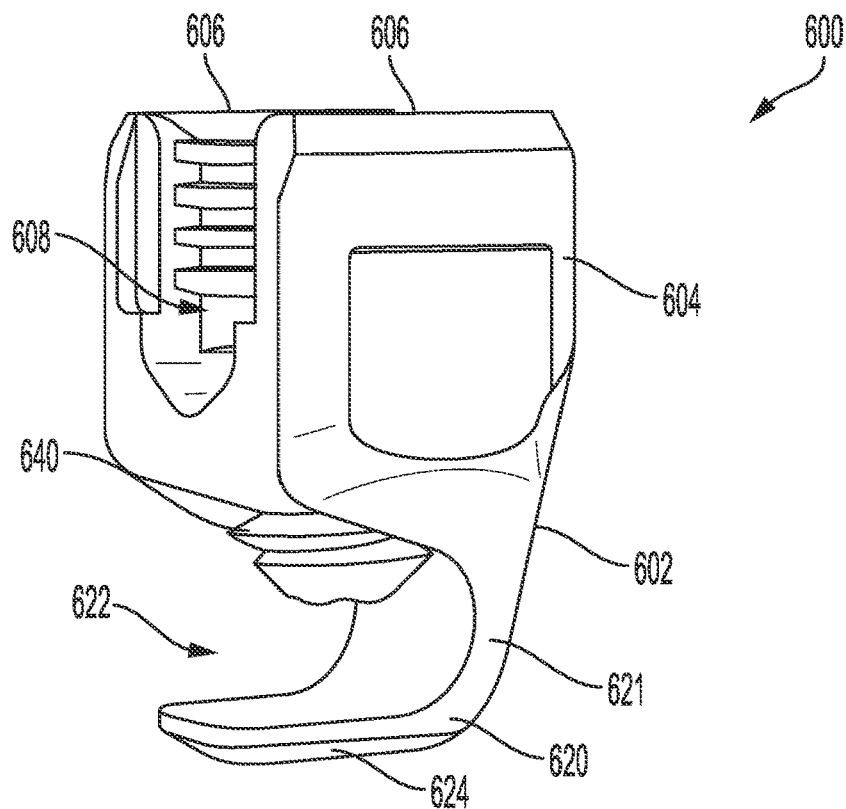
FIG. 6A is a perspective view of another embodiment of a spinal fixation system component.
Figure 6B:
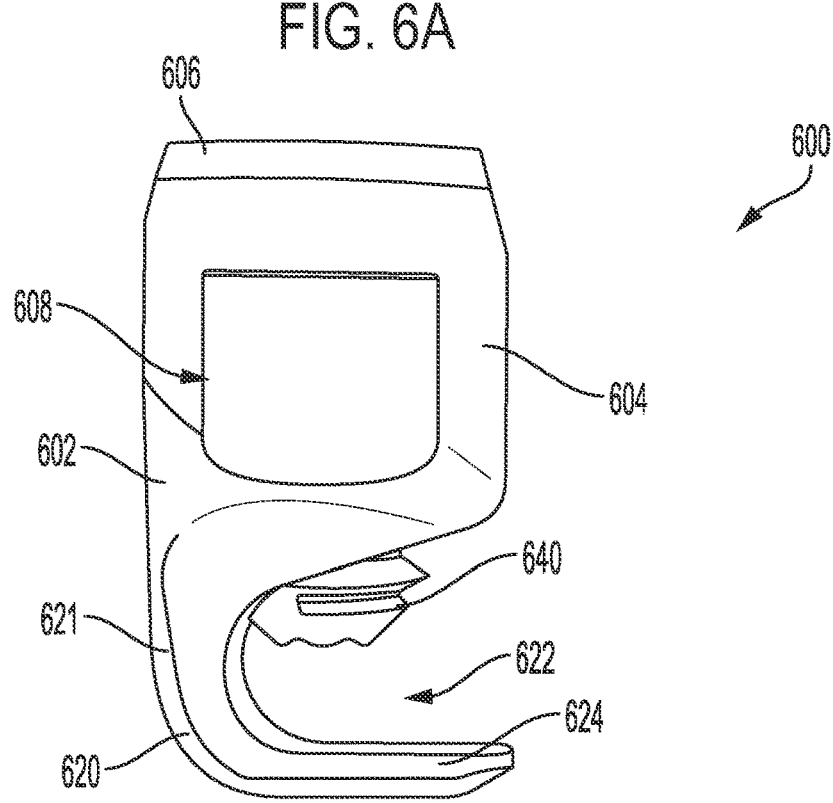
FIG. 6B is a side view of the spinal fixation system component of FIG. 6A.
Figure 6C:
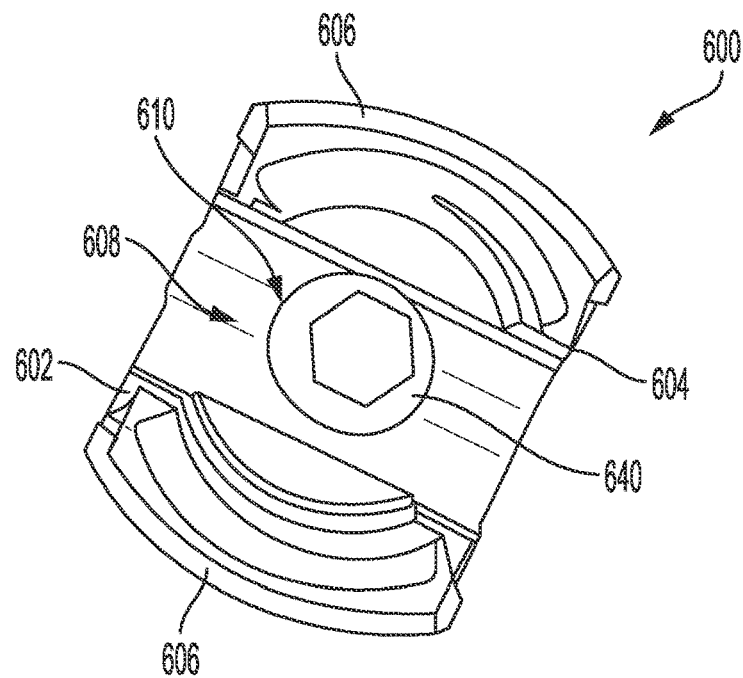
FIG. 6C is a top down view of the spinal fixation system component of FIG. 6A.

In addition to closing an opening in a hook member or moving a hook member relative to a receiver head, another mechanism for securing a hook member to spinal anatomy without spinal anatomy penetration can include using a screw or pin to engage a portion of spinal anatomy, such as lamina, in the opening of the hook member. For example, FIGS. 6A-6C illustrate another embodiment of a spinal fixation system 600 that is similar to the spinal fixation systems above, but it includes a screw 640 that is configured to secure the spinal fixation system 600 to a portion of spinal anatomy, such as lamina. The spinal fixation system 600 has a receiver 602 with a receiver head 604 and a hook member 620, and the hook member 620 extends distally from the receiver head 604 and defines an opening 622 that is configured to receive spinal anatomy in an open portion thereof. The screw 640 is configured to extend into the opening 622 such that, when the spinal anatomy is received in the opening 622, the screw 640 is configured to be tightened against the spinal anatomy to secure the spinal anatomy in the opening 622, and thus to secure the hook member 620 to the spinal anatomy, without penetrating the spinal anatomy.

The receiver head 604 is configured to receive various spinal fixation members, such as a spinal rod. As such, the receiver head 604 has opposed arms 606 on a distal end thereof with a channel 608 between the arms 606 that is configured to receive a spinal fixation member. The opposed arms 606 have threading on surfaces facing the channel 608 that is configured to engage with various closure members, such as a set screw, after a spinal fixation member is received therein, and the various closure members are separate from the screw 640.

Furthermore, the receiver head 604 is configured to allow the screw 640 to extend therefrom into the opening 622 to secure spinal anatomy in the opening 622. A threaded opening 610 is defined in a base of the receiver head 604 that is in communication with the channel 608 and the opening 622, and it is configured to receive the screw 640 therethrough. The opening 610 is positioned below any contacting surface of any spinal fixation member so as not to interfere with placement of spinal fixation members in the channel 608.

As noted, the hook member 620 is of a shape that defines an opening that is configured to receive spinal anatomy therein. The hook member 620 includes a hook arm 621 that extends distally from the receiver head 604 and a blade 624 at a distal end of the hook arm that extends at an angle relative to the hook arm to define one edge of the opening 622. While the illustrated angle of the blade 624 is approximately 90 degrees, it can extend at a variety of angles similar to the angle α discussed above with respect to FIGS. 1A-1E. The blade 624 has a bone-engaging surface 628 thereon that faces spinal anatomy received in the opening 622. In the illustrated embodiment, the hook member 620 is integral with the receiver head 604, however one skilled in the art will appreciate that the hook member 620 can be formed separately. While the bone-engaging surface 628 is smooth in FIGS. 6A-6C, the bone engaging surface can be rougher than surrounding surfaces to better grip the spinal anatomy, such as having a textured surface that results from a process such as grit-blasting.

As noted, the screw 640 is configured to extend into the opening 622 and secure spinal anatomy therein, however the screw 640 is configured not to penetrate spinal anatomy. Rather, the screw 640 is configured to apply a distally directed force to spinal anatomy to secure the spinal anatomy between a distal tip of the screw 640 and the bone-engaging surface 628 of the blade 624. The screw 640 is a flat-bottomed screw that, when secured against spinal anatomy, has a driver head on a distal end thereof that is configured to sit below any contacting surface of any spinal fixation members in the channel 608. The driver head of the screw is configured to receive a tool therein to rotate the screw into or out of the opening 622.

While the screw 640 is discussed above is useful in one embodiment, various other protuberances can be used to secure spinal anatomy in the opening, for example pins, bumps, columns, and the like. When using one or more of these alternative embodiments, a saddle can also be placed in the bottom of the channel to receive a spinal fixation member thereon and force the pin, bump, etc. proximally into secured engagement with the spinal anatomy. Various springs, friction-fit locking mechanisms, and the like can also be used to provide distal pressure on the pin, bump, etc. to maintain engagement with spinal anatomy.

In use, the spinal fixation system 600 is used similar to the systems discussed above. However, when a selected portion of the spinal anatomy, such as the lamina is inserted into the opening 622 of the hook member 620, the screw 640 is driven into the opening 622 and pressed against the spinal anatomy to secure the spinal anatomy between the flat distal tip of the screw 640 and the blade 624 of the hook member 620. Once the screw 640 is tightened against the spinal anatomy, the receiver 602 is secured on the spinal anatomy. A spinal fixation member, such as a spinal rod, is then inserted into the channel 608 and a closure member, such as a set screw, is threaded between the opposed arms 606.

Figure 7A:
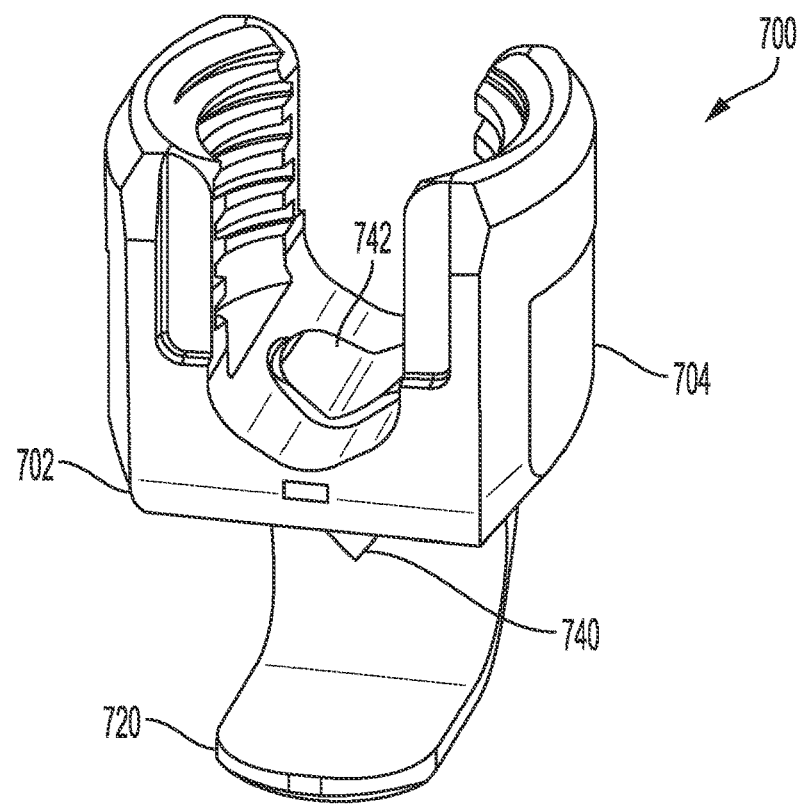
FIG. 7A is a perspective view of another embodiment of a spinal fixation system component.
Figure 7B:
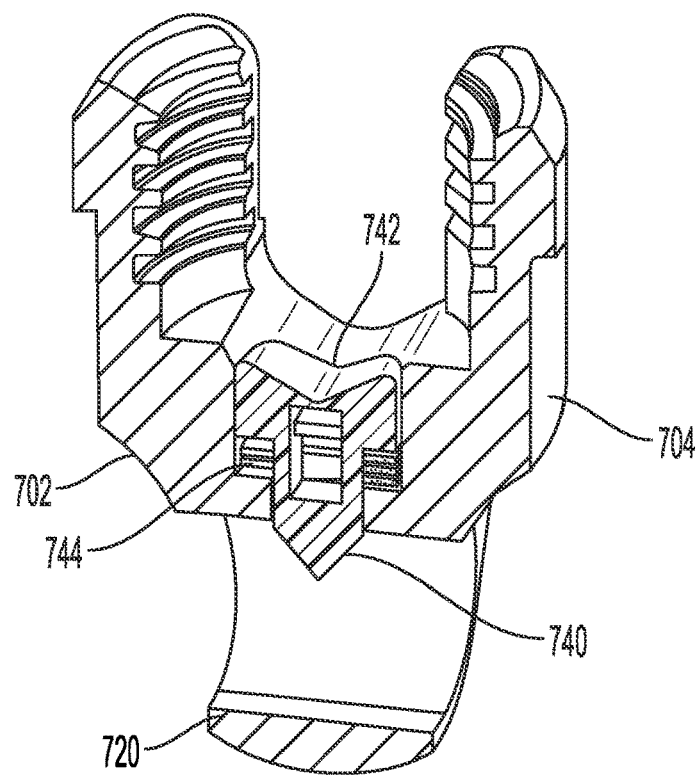
FIG. 7B is a side view of the spinal fixation system component of FIG. 7A.
Figure 7C:
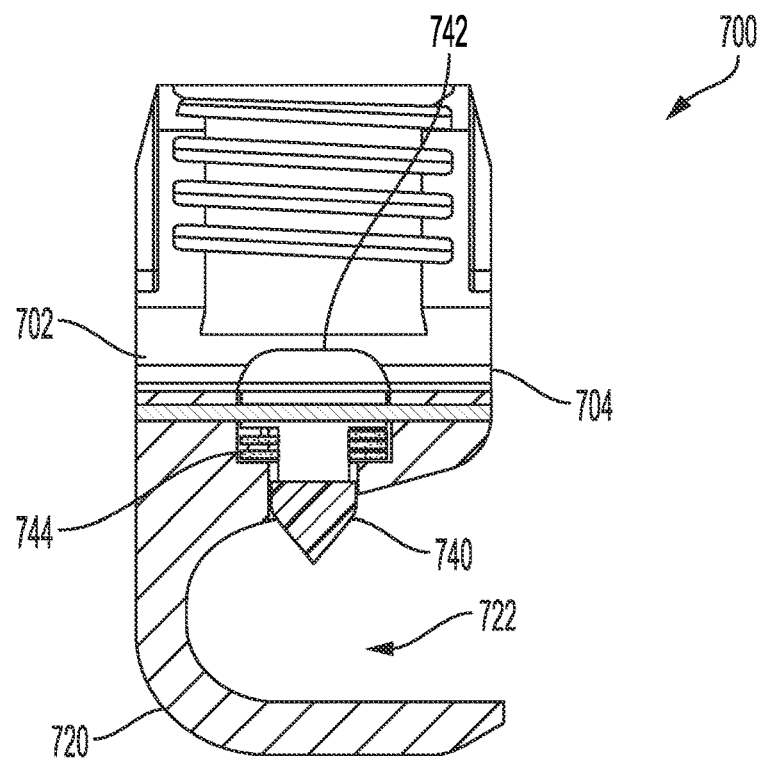
FIG. 7C is a top down view of the spinal fixation system component of FIG. 7A.

While the screw 640 and the various protuberances discussed above are configured not to penetrate bone, a spinal fixation system 700 similar to the system 600 can be used with a pin 740 or screw that is configured to penetrate bone. As illustrated in FIGS. 7A-7C, the spinal fixation system 700 has a receiver 702 with a receiver head 704 and a hook member 720, and the hook member 720 extends distally from the receiver head 704 and defines an opening 722 that is configured to receive spinal anatomy in an open portion thereof. The pin 740 is configured to extend into the opening 722 such that, when the spinal anatomy is received in the opening 722, the pin 740 can be driven through an opening or channel in the receiver head 704 into the opening 722 and pressed against the spinal anatomy to secure the spinal anatomy between a distal tip of the pin 740 and a blade of the hook member. However, during placement, the pin 740 at least partially penetrates the spinal anatomy, thus securing the hook member 700 and the receiver 700 generally to the spinal anatomy in a secure fit. As illustrated, the pin 740 has an upper saddle 742 that is configured to sit in the receiver head 704. A spring 744 sits between the upper saddle 742 and the receiver head 704 to keep the saddle 742 biased proximally out of engagement with any spinal anatomy in the opening 722. When a spinal fixation member, such as a spinal rod, is inserted into the receiver head 704 and tightened into place, however, the spinal fixation member sits on the saddle 742 and forces the pin 740 distally into the opening 722 as it overcomes the spring bias. The sharp distal point of the pin 740 is thus forced distally into spinal anatomy in the opening to cause the pin 740 to at least partially penetrate the spinal anatomy therein and secure the receiver 702 to the spinal anatomy. Other embodiments can use other protuberances that are configured to penetrate bone in much the same way as the pin 740, such as screws. For example, in some embodiments, a receiver similar to the receiver 602 discussed above can incorporate a screw with a distal point that penetrates into spinal anatomy during placement.

The devices disclosed herein can be designed to be disposed of after a single use, or they can be designed to be used multiple times. The device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices and components described herein may be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A spinal fixation system, comprising:
a receiver having first and second ends, the first end having a pair of opposed arms and a channel therebetween configured to receive at least one fixation member, the second end being angularly offset from the first end;
a hook member operably coupled to the second end of the receiver such that the hook member is angularly offset with the first end, the hook member having an opening configured to receive a portion of spinal anatomy therein, the hook member being configured to be movable relative to the receiver between an open position allowing removal of the portion of spinal anatomy and a closed position securing the receiver to the portion of spinal anatomy through non-penetrative force; and
a closure member insertable between the opposed arms of the receiver and configured to compress the fixation member into the receiver.

2. The spinal fixation system of claim 1, further comprising a coupling member coupling the receiver to the hook member, the coupling member being configured to be rotated to move the hook member between the open and closed positions.

3. The spinal fixation system of claim 1, wherein the hook member is configured to move away from the receiver in the open position and toward the receiver in the closed position.

4. The spinal fixation system of claim 1, wherein the hook member has a blade on a distal end thereof, and the blade has a bone engagement surface configured to grip the bone between the bone engagement surface and the receiver in the closed position.

5. The spinal fixation system of claim 4, wherein the bone engagement surface is rougher than surrounding surfaces of the hook member.

6. The spinal fixation system of claim 1, wherein the receiver has a hook engagement portion configured to facilitate engagement between the hook member and the receiver, and configured to cause the hook member to move between the open and closed positions.

7. The spinal fixation system of claim 6, further comprising a cavity extending through the hook engagement portion, and a channel extending through the hook member, the cavity and the channel being axially aligned relative to each other; and
    a threaded shaft extending through the cavity and the channel, the threaded shaft configured to engage each of the cavity and the channel such that rotation of the threaded shaft causes the hook member to move between the open and closed positions.

8. The spinal fixation system of claim 7, wherein an inner surface of the channel of the hook member is at least partially threaded to engage with corresponding threads on the threaded shaft, and the hook member is configured to move proximally to the closed position and distally to the open position with respect to the receiver upon rotation of the threaded shaft in first and second directions.

9. The spinal fixation system of claim 7, wherein the threaded shaft has a swage distal end configured to engage a distal end of the channel of the hook member.

10. A spinal fixation system, comprising:
    a receiver having first and second ends, the first end having a pair of opposed arms and a channel therebetween configured to receive at least one fixation member, the second end being angularly offset from the first end;
    a bone engagement mechanism movably engaged with the second end of the receiver such that the bone engagement mechanism is angularly offset from the first end, and configured to receive a bone therein, the bone engagement mechanism having a compression member extending therethrough, the compression member being configured to cause proximal movement of the bone engagement mechanism relative to the receiver to apply non-penetrative gripping force to the bone therein, and configured to cause distal movement of the bone engagement mechanism relative to the receiver to release the bone therefrom; and
    a closure member insertable between the opposed arms of the receiver and configured to compress the fixation member into the receiver.

11. The spinal fixation system of claim 10, wherein the compression member comprises a threaded shaft extending between the receiver and the bone engagement mechanism.

12. The spinal fixation system of claim 11, wherein the threaded shaft is configured to cause proximal and distal movement of the bone engagement mechanism based on rotation thereof.

13. The spinal fixation system of claim 10, wherein the bone engagement mechanism has a blade on a distal end thereof, and the blade has a bone engagement surface configured to grip the bone between the bone engagement surface and the receiver when the bone engagement mechanism moves proximally relative to the receiver.

14. The spinal fixation system of claim 13, wherein the bone engagement surface is rougher than surrounding surfaces of the bone engagement mechanism.

15. A spinal fixation method, comprising:
    placing an open portion of a bone engagement mechanism on a distal end of a receiver of a surgical device into engagement with a portion of a vertebra;
    rotating a closure member on the bone engagement mechanism to move the bone engagement mechanism from an open position allowing release of the portion of the vertebra to a closed position gripping the vertebra between the bone engagement mechanism and the receiver without penetrating the vertebra;
    inserting a spinal rod into a channel defined by opposed arms on a proximal end of the receiver of the surgical device, the proximal end of the receiver being angularly offset from the distal end of the receiver such that the bone engagement mechanism is angularly offset from the proximal end; and
    rotating a set screw between the opposed arms to secure the spinal rod into the channel.

16. The spinal fixation method of claim 15, wherein rotating the closure member causes a blade on a distal end of the hook member to move proximally from the open position to the closed position to grip the vertebra.

17. The spinal fixation method of claim 15, wherein rotating the closure member causes rotation of a threaded shaft extending between the receiver and the hook member to move the hook member between the open and closed positions.

* * * * *